United States Patent
Blythe et al.

(10) Patent No.: US 8,388,821 B2
(45) Date of Patent: Mar. 5, 2013

(54) METHOD FOR DETERMINING HEMATOCRIT CORRECTED ANALYTE CONCENTRATIONS

(75) Inventors: Stephen Patrick Blythe, Inverness (SE); Marco F. Cardosi, Croy (GB); Andrew Gill, Alloa (GB); Leanne Mills, Inverness (GB); Christopher Philip Leach, Inverness (GB)

(73) Assignee: LifeScan Scotland Limited (GB)

( * ) Notice: Subject to any disclaimer, the term of this patent is extended or adjusted under 35 U.S.C. 154(b) by 657 days.

(21) Appl. No.: 12/305,363

(22) PCT Filed: Oct. 5, 2007

(86) PCT No.: PCT/GB2007/003770
§ 371 (c)(1),
(2), (4) Date: Dec. 1, 2009

(87) PCT Pub. No.: WO2008/040982
PCT Pub. Date: Apr. 10, 2008

(65) Prior Publication Data
US 2010/0219084 A1   Sep. 2, 2010

Related U.S. Application Data

(60) Provisional application No. 60/850,173, filed on Oct. 5, 2006.

(51) Int. Cl.
*G01N 27/327* (2006.01)
(52) U.S. Cl. .................. 204/403.02; 205/777.5; 435/25
(58) Field of Classification Search .................. 205/775, 205/777.5, 778, 792; 204/403.01–403.15; 435/4, 14, 25–28; 600/345, 347
See application file for complete search history.

(56) References Cited

U.S. PATENT DOCUMENTS
(Continued)

FOREIGN PATENT DOCUMENTS
AU   2006200073 A1   2/2006
EP     0928967 A     7/1999
(Continued)

OTHER PUBLICATIONS

L. Chen, et al., "Bioinorganic composites for enzyme electrodes", vol. 73, No. 13, pp. 2862-2868, XP002463785, Jul. 1, 2001.

(Continued)

*Primary Examiner* — J. Christopher Ball

(57) ABSTRACT

Description is provided herein for an embodiment of a method determining a hematocrit-corrected glucose concentration. The exemplary method includes providing a test strip having a reference electrode and a working electrode, wherein the working electrode includes a plurality of microelectrodes and is coated with at least an enzyme and a mediator. The method can be achieved by: providing a test strip comprising a reference electrode and a working electrode formed with a plurality of microelectrodes and coated with a reagent layer; applying a fluid sample to the test strip for a reaction period; applying a test voltage between the reference electrode and the working electrode; measuring a test current as a function of time; measuring a steady state current value when the test current has reached an equilibrium; calculating a ratio of the test current to the steady state current value; plotting the ratio of the test current to the steady state current value as a function of the inverse square root of time; calculating an effective diffusion coefficient from the slope of the linearly regressed plot of the ratio of the test current to the steady state current value as a function of the inverse square root of time; and calculating a hematocrit-corrected concentration of analyte.

15 Claims, 16 Drawing Sheets

U.S. PATENT DOCUMENTS

| | | |
|---|---|---|
| 5,312,590 A | 5/1994 | Gunasingham |
| 5,653,918 A | 8/1997 | Towlson et al. |
| 5,708,247 A | 1/1998 | McAleer et al. |
| 6,046,051 A | 4/2000 | Jina |
| 6,179,979 B1 | 1/2001 | Hodges et al. |
| 6,241,862 B1 | 6/2001 | McAleer et al. |
| 6,448,794 B1 | 9/2002 | Cheng et al. |
| 6,511,592 B1 * | 1/2003 | Hill et al. .................. 205/777.5 |
| 7,112,265 B1 | 9/2006 | McAleer et al. |
| 2003/0116447 A1 | 6/2003 | Surridge et al. |
| 2003/0143113 A2 | 7/2003 | Yuzhakov et al. |
| 2003/0217918 A1 | 11/2003 | Davies et al. |
| 2004/0096959 A1 | 5/2004 | Stiene et al. |
| 2004/0260511 A1 | 12/2004 | Burke et al. |
| 2005/0096409 A1 | 5/2005 | Davies et al. |

FOREIGN PATENT DOCUMENTS

| | | |
|---|---|---|
| EP | 1156324 A | 11/2001 |
| EP | 1318399 A | 6/2003 |
| EP | 1426757 A | 6/2004 |
| EP | 1447660 A | 8/2004 |
| EP | 1467206 A | 10/2004 |
| EP | 1496354 A | 1/2005 |
| EP | 1775587 A | 4/2007 |
| EP | 1839571 A | 10/2007 |
| EP | 1840219 A | 10/2007 |
| WO | WO 01/67099 A1 | 9/2001 |
| WO | WO 01/73124 A2 | 10/2001 |
| WO | WO 02/49507 A1 | 6/2002 |
| WO | WO 03/097860 A | 11/2003 |
| WO | WO 2004/039600 A2 | 5/2004 |
| WO | WO 2004/039897 A2 | 5/2004 |
| WO | WO 2004/040005 A1 | 5/2004 |
| WO | WO 2004/040285 A1 | 5/2004 |
| WO | WO 2004/040287 A1 | 5/2004 |
| WO | WO 2004/040290 A1 | 5/2004 |
| WO | WO 2004/040948 A1 | 5/2004 |
| WO | WO 2005/045414 A | 5/2005 |
| WO | WO 2006/057722 A | 6/2006 |
| WO | WO 2006/072089 A | 7/2006 |

OTHER PUBLICATIONS

PCT Search Report, PCT patent application No. PCT/GB2007/003791, dated Oct. 4, 2008, 4 pages.

PCT Search Report, PCT patent application No. PCT/GB2007/003770, dated Jan. 16, 2008, 3 pages.

PCT Search Report, PCT patent application No. PCT/GB2007/003781, dated Mar. 25, 2008, 3 pages.

PCT Search Report, PCT patent application No. PCT/GB2007/003790, dated Jan. 25, 2008, 2 pages.

PCT Search Report, PCT patent application No. PCT/GB2007/003772, dated Jan. 21, 2008, 3 pages.

* cited by examiner

METHOD FOR DETERMINING HEMATOCRIT CORRECTED ANALYTE CONCENTRATIONS

PRIORITY

This application claims the benefits of priority under 35 U.S.C. §119 from provisional application Ser. No. 60/850,173 filed on Oct. 5, 2006, entitled: "Method for Determining Hematocrit Corrected Analyte Concentrations," which application is incorporated by reference in its entirety herein.

BACKGROUND OF THE INVENTION

Electrochemical glucose test strips, such as those used in the OneTouch® Ultra® whole blood testing kit, which is available from LifeScan, Inc., are designed to measure the concentration of glucose in a blood sample from patients with diabetes. The measurement of glucose is based upon the specific oxidation of glucose by the flavo-enzyme glucose oxidase. The reactions which may occur in a glucose test strip are summarized below in Equations 1 and 2.

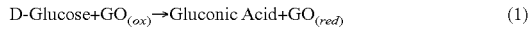
(1)

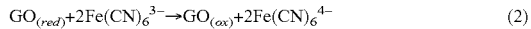
(2)

As shown in Equation 1, glucose is oxidized to gluconic acid by the oxidized form of glucose oxidase ($GO_{(ox)}$). It should be noted that $GO_{(ox)}$ may also be referred to as an "oxidized enzyme". During the reaction in Equation 1, the oxidized enzyme $GO_{(ox)}$ is converted to its reduced state which is denoted as $GO_{(red)}$ (i.e., "reduced enzyme"). Next, the reduced enzyme $GO_{(red)}$ is re-oxidized back to $GO_{(ox)}$ by reaction with $Fe(CN)_6^{3-}$ (referred to as either the oxidized mediator or ferricyanide) as shown in Equation 2. During the re-generation of $GO_{(ox)}$ back to its oxidized state $GO(CN)_6^{3-}$ is reduced to $Fe(CN)_6^{4-}$ (referred to as either reduced mediator or ferrocyanide).

When the reactions set forth above are conducted with a test voltage applied between two electrodes, a test current may be created by the electrochemical re-oxidation of the reduced mediator at the electrode surface. Thus, since, in an ideal environment, the amount of ferrocyanide created during the chemical reaction described above is directly proportional to the amount of glucose in the sample positioned between the electrodes, the test current generated would be proportional to the glucose content of the sample. A mediator, such as ferricyanide, is a compound that accepts electrons from an enzyme such as glucose oxidase and then donates the electrons to an electrode. As the concentration of glucose in the sample increases, the amount of reduced mediator formed also increases, hence, there is a direct relationship between the test current resulting from the re-oxidation of reduced mediator and glucose concentration. In particular, the transfer of electrons across the electrical interface results in a flow of test current (2 moles of electrons for every mole of glucose that is oxidized). The test current resulting from the introduction of glucose may, therefore, be referred to as a glucose current.

Because it can be very important to know the concentration of glucose in blood, particularly in people with diabetes, test meters have been developed using the principals set forth above to enable the average person to sample and test their blood to determine the glucose concentration at any given time. The glucose current generated is monitored by the test meter and converted into a reading of glucose concentration using an algorithm that relates the test current to a glucose concentration via a simple mathematical formula. In general, the test meters work in conjunction with a disposable test strip that includes a sample receiving chamber and at least two electrodes disposed within the sample receiving chamber in addition to the enzyme (e.g. glucose oxidase) and the mediator (e.g. ferricyanide). In use, the user pricks their finger or other convenient site to induce bleeding and introduces a blood sample to the sample receiving chamber, thus starting the chemical reaction set forth above.

In electrochemical terms, the function of the meter is two fold. Firstly, it provides a polarizing voltage (approximately 0.4 V in the case of OneTouch® Ultra®) that polarizes the electrical interface and allows current flow at the carbon working electrode surface. Secondly, it measures the current that flows in the external circuit between the anode (working electrode) and the cathode (reference electrode). The test meter may, therefore be considered to be a simple electrochemical system that operates in a two-electrode mode although, in practice, third and, even fourth electrodes may be used to facilitate the measurement of glucose and/or perform other functions in the meter.

In most situations, the equation set forth above is considered to be a sufficient approximation of the chemical reaction taking place on the test strip and the test meter outputting a sufficiently accurate representation of the glucose content of the blood sample. However, under certain circumstances and for certain purposes, it may be advantageous to improve the accuracy of the measurement. For example, blood samples having a high hematocrit level or low hematocrit level may cause a glucose measurement to be inaccurate.

A hematocrit level represents a percentage of the volume of a whole blood sample occupied by red blood cells. The hematocrit level may also be represented as a fraction of red blood cells present in a whole blood sample. In general, a high hematocrit blood sample is more viscous (up to about 10 centipoise at 70% hematocrit) than a low hematocrit blood sample (about 3 centipoise at 20% hematocrit). In addition, a high hematocrit blood sample has a higher oxygen content than low hematocrit blood because of the concomitant increase in hemoglobin, which is a carrier for oxygen. Thus, the hematocrit level can influence the viscosity and oxygen content of blood. As will be later described, both viscosity and oxygen content may change the magnitude of the glucose current and in turn cause the glucose concentration to be inaccurate.

A high viscosity sample (i.e., high hematocrit blood sample) can cause the test current to decrease for a variety of factors such as a decrease in 1) the dissolution rate of enzyme and/or mediator, 2) the enzyme reaction rate, and 3) the diffusion of a reduced mediator towards the working electrode. A decrease in current that is not based on a decrease in glucose concentration can potentially cause an inaccurate glucose concentration to be measured.

A slower dissolution rate of the reagent layer can slow down the enzymatic reaction as shown in Equations 1 and 2 because the oxidized enzyme $GO_{(ox)}$ must dissolve first before it can react with glucose. Similarly, ferricyanide ($Fe(CN)_6^{3-}$) must dissolve first before it can react with reduced enzyme $GO_{(red)}$. If the undissolved oxidized enzyme $GO_{(ox)}$ cannot oxidize glucose, then the reduced enzyme $GO_{(red)}$ cannot produce the reduced mediator $Fe(CN)_6^{4-}$ needed to generate the test current. Further, oxidized enzyme $GO_{(ox)}$ will react with glucose and oxidized mediator $Fe(CN)_6^{3-}$ more slowly if it is in a high viscosity sample as opposed to a low viscosity sample. The slower reaction rate with high viscosity samples is ascribed to an overall decrease in mass diffusion. Both oxidized enzyme $GO_{(ox)}$ and glucose must collide and interact together for the reaction to occur as shown in Equation 1. The ability of oxidized enzyme $GO_{(ox)}$ glucose to collide and interact together is slowed down when they are in a viscous sample. Yet further, reduced mediator $Fe(CN)_6^{4-}$ will diffuse to the working electrode slower when dissolved in a high viscosity sample. Because the test current is typically limited by the diffusion of reduced mediator $Fe(CN)_6^{4-}$ to the working electrode, a high viscosity sample will also attenuate the test current. In summary, there are several factors that cause the test current to decrease when the sample has an increased viscosity.

A high oxygen content may also cause a decrease in the test current. The reduced enzyme $(GO_{(red)})$ can reduce oxygen $(O_2)$ to hydrogen peroxide as shown be Equation 3.

$$GO_{(red)} + O_2 \rightarrow GO_{(ox)} + H_2O_2 \qquad (3)$$

As noted earlier, the reduced enzyme $GO_{(red)}$ can also reduce ferricyanide $(Fe(CN)_6^{3-})$ to ferrocyanide $(Fe(CN)_6^{4-})$ as shown in Equation 2. Thus, oxygen can compete with ferricyanide for reacting with the reduced enzyme $(GO_{(red)})$. In other words, the occurrence of the reaction in Equation 3 will likely cause a decrease in the rate of the reaction in Equation 2. Because of such a competition between ferricyanide and oxygen, a higher oxygen content will cause less ferrocyanide to be produced. In turn, a decrease in ferrocyanide would cause a decrease in the magnitude of the test current. Therefore, a high oxygen content blood sample can potentially decrease the test current and affect the accuracy of the glucose measurement.

As such, applicants have great interest in the development of methods reducing the effects of hematocrit on a glucose measurement. In certain protocols, a pre-cast blood filtering membrane that is separate from the reagent layer has been employed to remove red blood cells and thereby reduce the hematocrit effect. The pre-cast blood filtering membrane which is separated from the reagent layer can be disposed on the working electrode. The use of a discrete pre-cast blood filtering membrane is unsatisfactory in that it requires a more complex test strip, increased sample volume, and increased testing time. The blood filtering membrane retains a certain amount of blood that does not contact the working electrodes causing a need for a larger blood sample. In addition, a finite amount of time is needed for the blood to be filtered by the membrane causing an increase in the overall test times. Thus, applicants recognize that it would be advantageous to reduce the effects of hematocrit without using a pre-cast blood filtering membrane that is separate from the reagent layer.

In the prior art, the hematocrit effect may be reduced by applying multiple test voltages such as, for example, a sinusoidal test voltage. However, applying a sinusoidal test voltage results in a more complex and expensive test meter. Further, the test meter needs to measure the test currents accurately and precisely at pre-determined time intervals. The electronic components can be expensive and complicated for a test meter to accurately and precisely apply multiple test voltages.

Applicants realize that it would be advantageous to implement a system having a test meter that applies only one test voltage and a test strip that does not use a pre-cast membrane to reduce the effects of hematocrit. The system instead uses a test strip having a working electrode with a plurality of microelectrodes formed thereon. More particularly, applicants recognizes that it would be advantageous to develop an algorithm that mathematically processes the collected test current using one test voltage such that an accurate glucose concentration can be determined that reduces the effects of hematocrit.

Furthermore, applicants have determined that it would be beneficial to provide a mechanism whereby the test meter can differentiate between a bodily fluid, for example whole blood, and a control solution. Similarly, it would be beneficial to provide a method whereby a test meter can determine if a test strip includes a plurality of microelectrodes formed on a working electrode.

SUMMARY OF THE INVENTION

In one aspect, a method is provided for determining a hematocrit-corrected glucose concentration. The exemplary method includes providing a test strip having a reference electrode and a working electrode, wherein the working electrode includes a plurality of microelectrodes and is coated with at least an enzyme and a mediator. The method can be achieved by: providing a test strip comprising a reference electrode and a working electrode formed with a plurality of microelectrodes and coated with a reagent layer; applying a fluid sample to the test strip for a reaction period; applying a test voltage between the reference electrode and the working electrode; measuring a test current as a function of time; measuring a steady state current value when the test current has reached an equilibrium; calculating a ratio of the test current to the steady state current value; plotting the ratio of the test current to the steady state current value as a function of the inverse square root of time; calculating an effective diffusion coefficient from the slope of the linearly regressed plot of the ratio of the test current to the steady state current value as a function of the inverse square root of time; and calculating a hematocrit-corrected concentration of analyte.

In another aspect of the present invention, the exemplary method further includes steps for distinguishing between a bodily fluid and a control solution. The method includes comparing the calculated value of the effective diffusion coefficient to an acceptance range for either a bodily fluid or a control solution, depending on the sample applied to the test strip. If the calculated value is not within the acceptance range for bodily fluid or control solution, the test meter will not allow the user to proceed with testing and will display an appropriate error message.

In another aspect, a method of determining a type of fluid sample applied to the test strip is provided. The method can be achieved by: providing a test strip having a reference electrode and a working electrode, wherein the working electrode is formed with a plurality of microelectrodes and is coated with a reagent layer; applying a fluid sample to the test strip for a reaction period; applying a test voltage between the reference electrode and the working electrode; measuring a test current as a function of time; measuring a steady state current value when the test current has reached an equilibrium; calculating a ratio of the test current to the steady state current value; plotting the ratio of the test current to the steady state current value as a function of the inverse square root of time; calculating an effective diffusion coefficient from the slope of the linearly regressed plot of the ratio of the test current to the steady state current value as a function of the inverse square root of time; determining a type of a fluid sample applied to the test strip by comparing a measured value for the effective diffusion coefficient against an acceptance range for a bodily fluid and a control solution; and displaying an appropriate error message if the effective diffusion coefficient does not pass the acceptance range for the type of fluid sample applied to the test strip.

In yet another aspect of the present invention, the exemplary method further includes steps for determining if a test strip includes a microelectrode array. The method includes using the effective diffusion coefficient to calculate a temperature-corrected effective diffusion coefficient. The calculated value for the temperature-corrected effective diffusion coefficient is then compared to an acceptance range for a test strip that includes a plurality of microelectrodes. If the calculated value is within the acceptance range for test strips having a plurality of microelectrodes, the user may proceed with testing. However, if the calculated value is not within the acceptance range for test strips having a plurality of microelectrodes, an appropriate error message is displayed on the test meter and the test meter will not allow the user to proceed with testing.

BRIEF DESCRIPTION OF DRAWINGS

A better understanding of the features and advantages of the present invention will be obtained by reference to the following detailed description that sets forth illustrative embodiments, in which the principles of the invention are utilized, and the accompanying drawings of which.

as a function of $$\frac{1}{\sqrt{t}}$$

Figure 18:
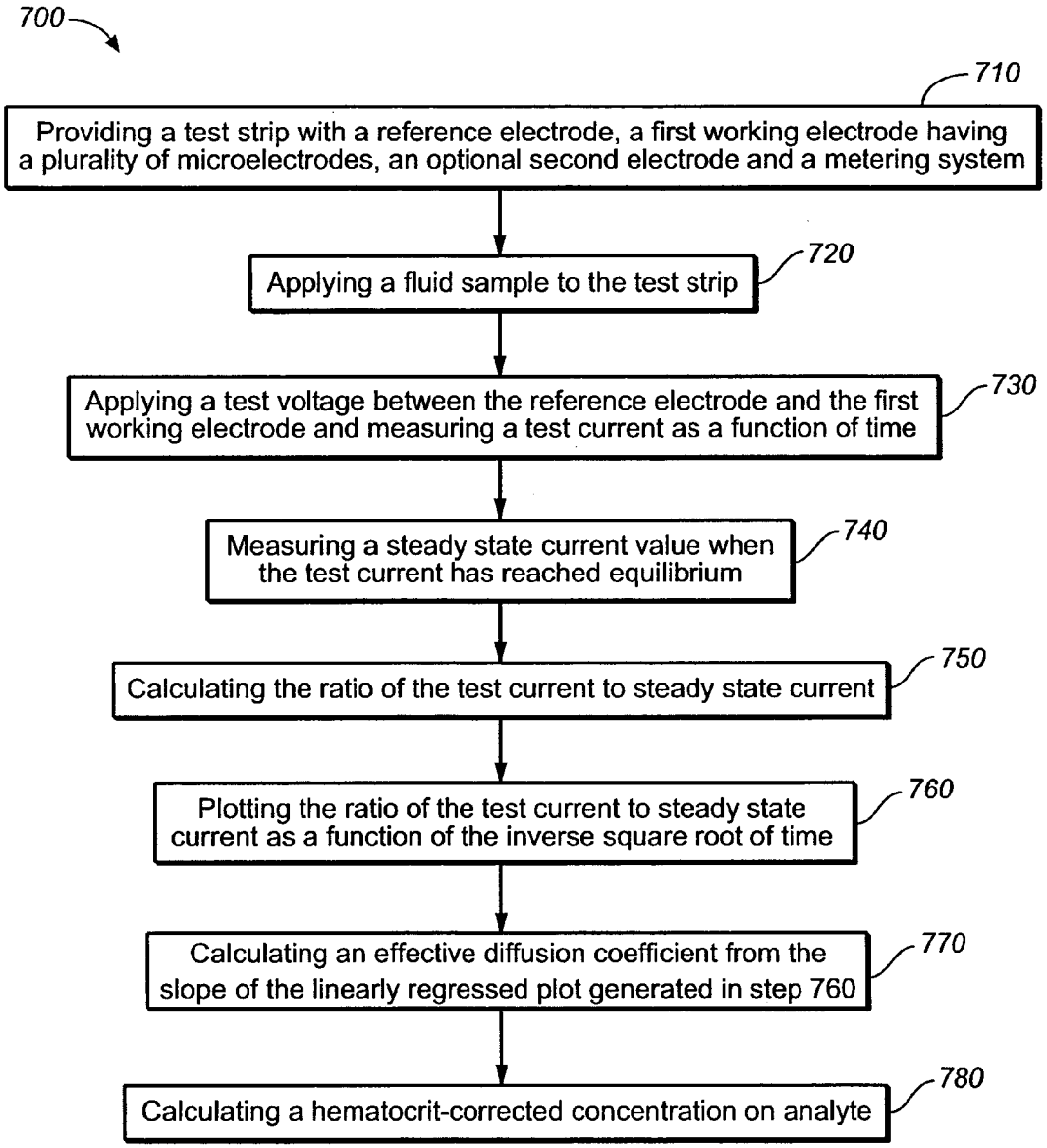
Figure 19:
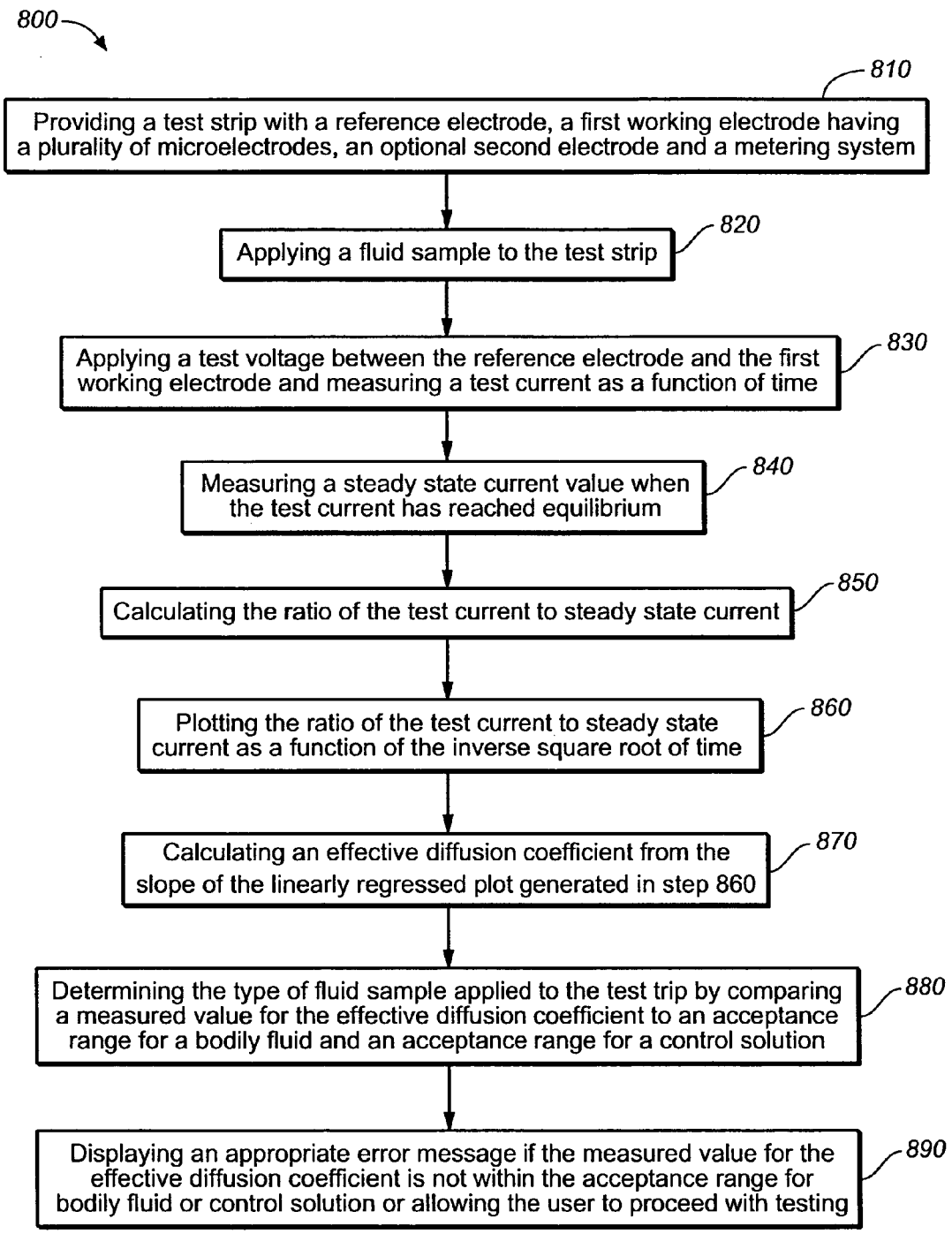
Figure 20:
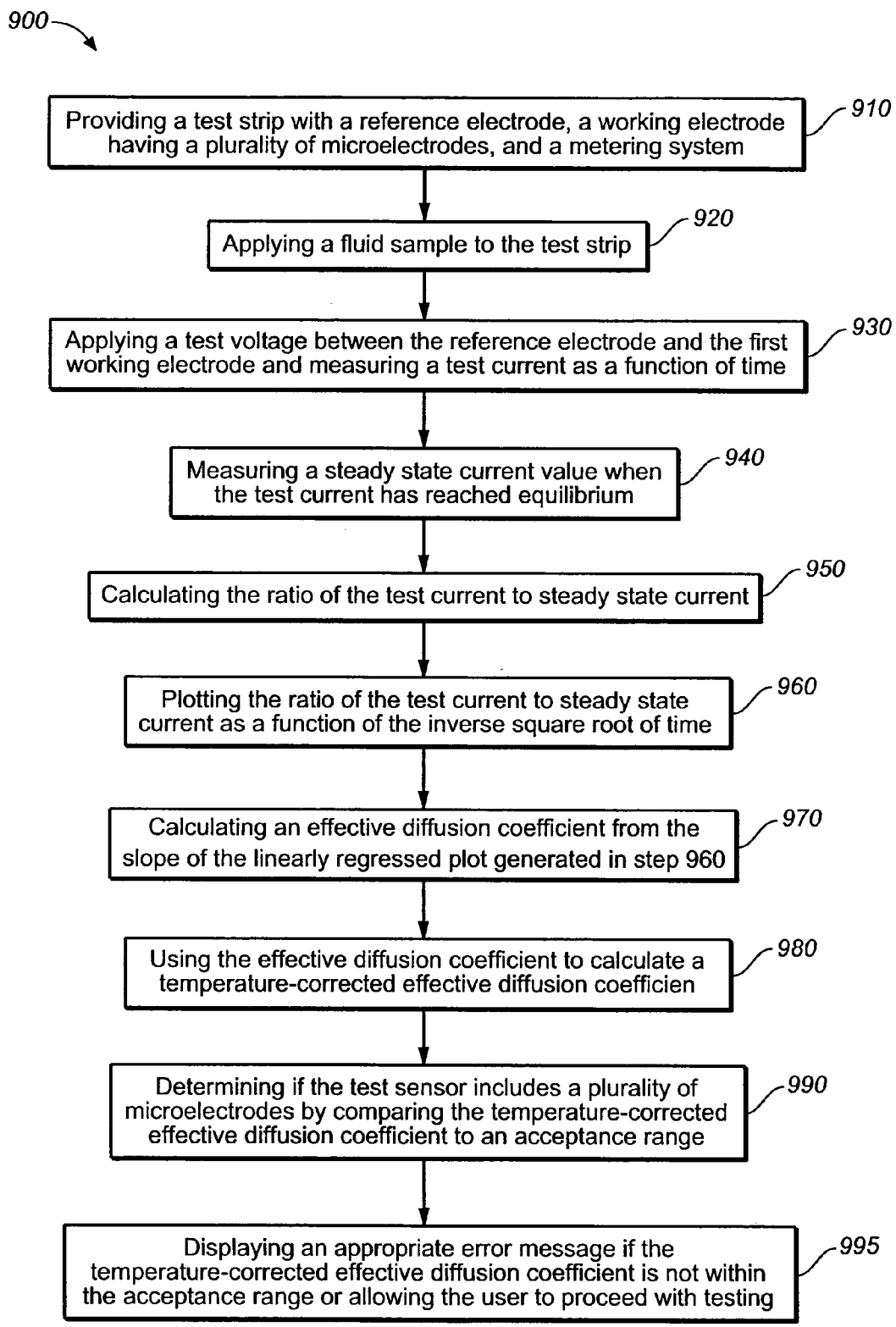
Figure 21:
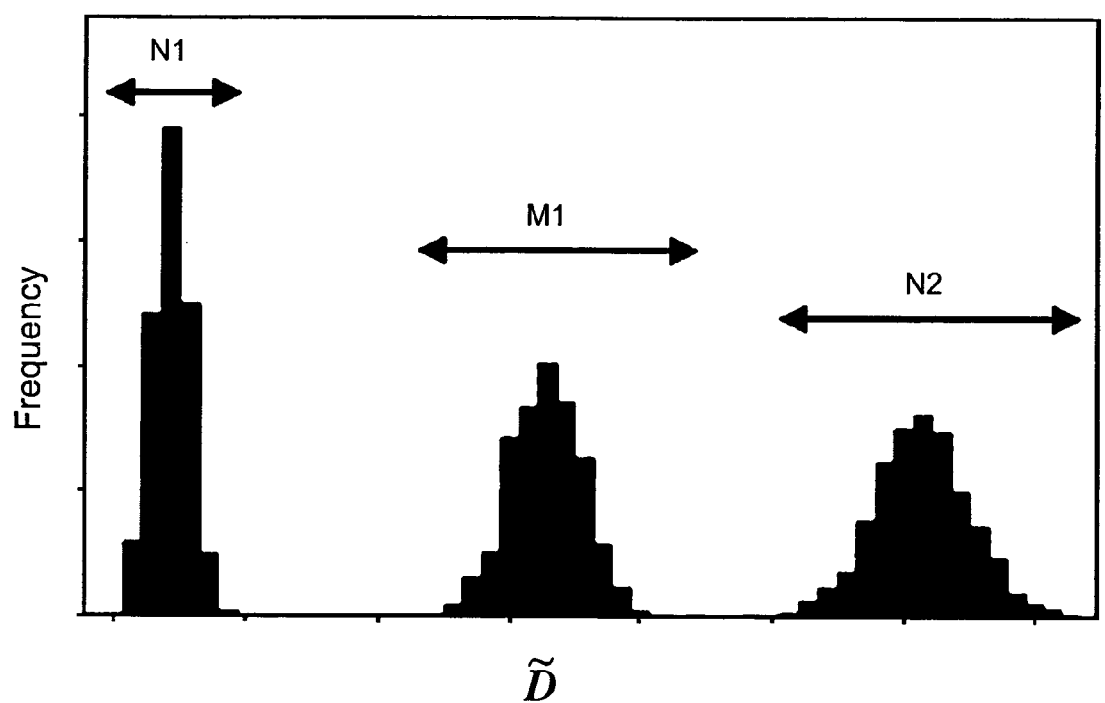
Figure 22:
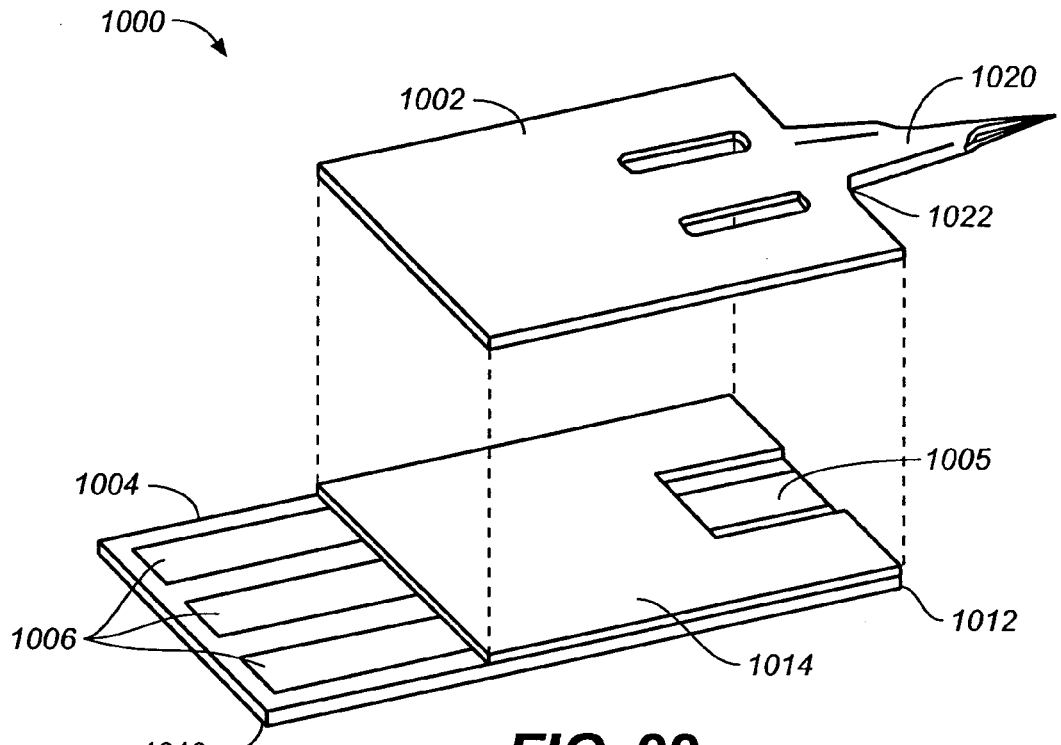
Figure 23:
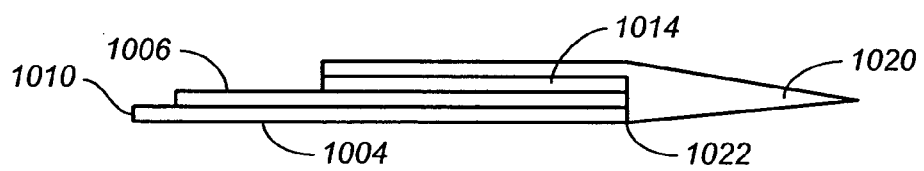

which is generated by a method;

FIG. 18 is a flowchart illustrating a sequence of steps in a method to determine a hematocrit-corrected analyte concentration reported by a test meter according to an exemplary embodiment;

FIG. 19 is a flowchart illustrating a sequence of steps in a method to determine whether a bodily fluid or a control solution has been added to a test strip according to an exemplary embodiment;

FIG. 20 is a flowchart illustrating a sequence of steps in a method to determine if a test strip includes a microelectrode array according to an exemplary embodiment;

FIG. 21 is a plot illustrating simulated data used to differentiate between a test strip that includes a microelectrode array and a test strip that does not include a microelectrode array, wherein the plot is generated by a method; and FIGS. 22 and 23 are perspective and side views, respectively, of a medical device that is suitable for use in the present invention.

DETAILED DESCRIPTION OF THE EXEMPLARY EMBODIMENTS

The disclosure below describes the measurement of a glucose concentration in a whole blood sample; however, the person of ordinary skill will recognize that the description is readily adapted to measure the properties of other analytes, such as cholesterol, ketone bodies or alcohol, and to other fluids such as saliva, urine, interstitial fluid, or test strip control solutions.

It will be further understood that this invention is not limited to only correcting for hematocrit and can also be applicable to correcting for the effect of variable viscosity or oxygen content in fluid samples. For example, whole blood samples can have a high viscosity for a variety of other reasons in addition to high hematocrit including low temperature (e.g., about 10° C.), high lipid concentration, and/or high protein concentration.

It will yet further be understood that the invention would also be applicable for reducing the effects caused by oxygen and/or viscosity of physiological fluids other than blood. For example, physiological fluids may also include plasma, serum, interstitial fluid, and a combination thereof. It should be noted that it is not uncommon for extracted interstitial fluid samples to be partially mixed with blood.

Figure 1:
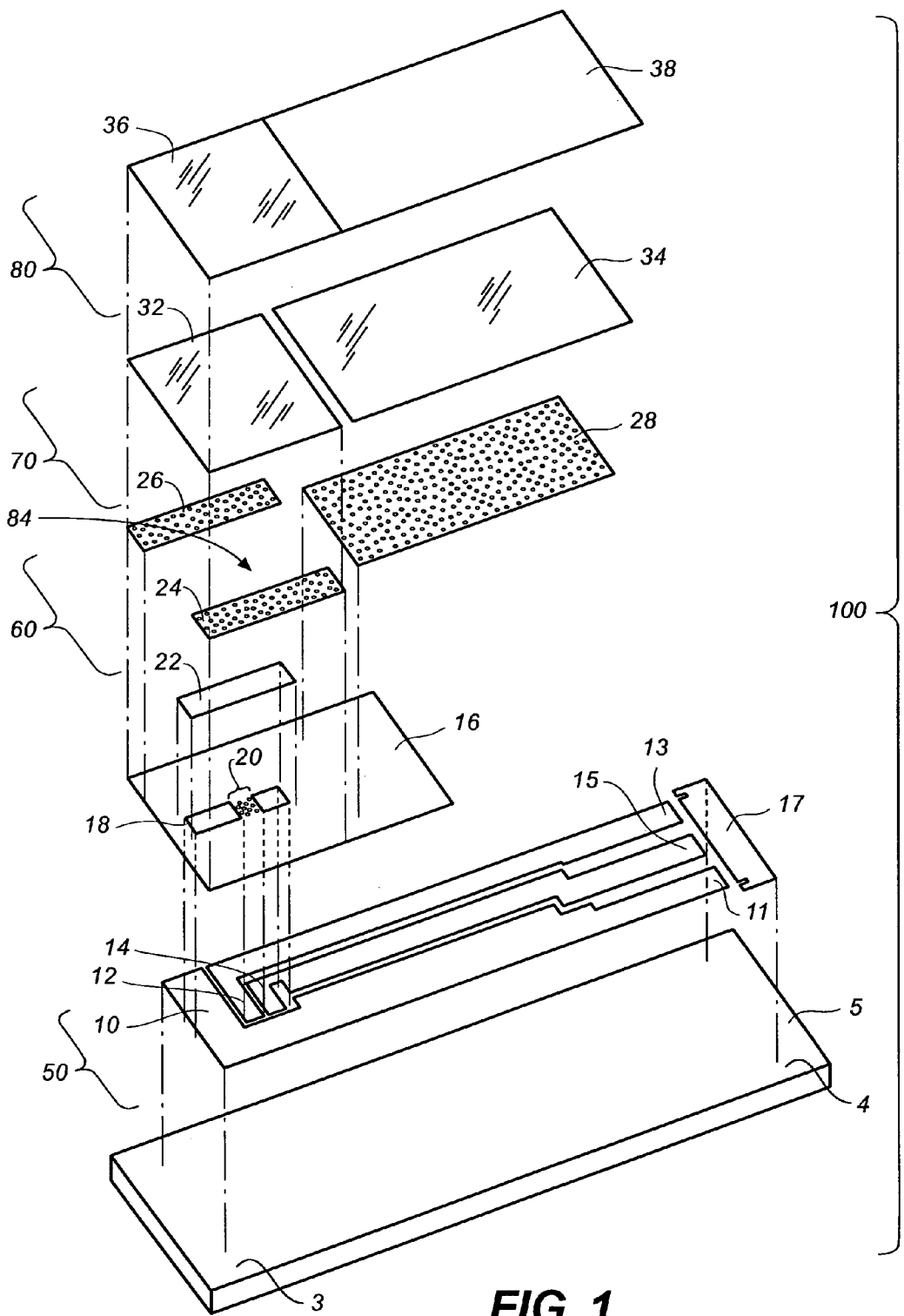
FIG. 1 is a top exploded perspective view of an unassembled test strip according to an exemplary embodiment of the present invention.

The following sections will describe a test strip embodiment that may be used with an algorithm according to one embodiment for calculating a hematocrit-corrected glucose concentration. FIG. 1 is an exploded perspective view of a test strip 100, which includes multiple layers disposed upon a substrate 5. These layers may include a conductive layer 50, an insulation layer 16, a reagent layer 22, an adhesive layer 60, a hydrophilic layer 70, and a top layer 80. Test strip 100 may be manufactured in a series of steps wherein conductive layer 50, insulation layer 16, reagent layer 22 and adhesive layer 60 are sequentially deposited on substrate 5 using, for example, a screen printing process as described in U.S. Pre-Grant Publication No. US20050096409A1 and published International Application No.'s WO2004040948A1, WO2004040290A1, WO2004040287A1, WO2004040285A2, WO2004040005A1, WO2004039897A2, and WO2004039600A2. In an alternative embodiment, an ink jetting process may be used to deposit reagent layer 22 on substrate 5. An example ink jetting process is described in U.S. Pat. No. 6,179,979. Hydrophilic layer 70 and top layer 80 may be disposed from a roll stock and laminated onto substrate 5. Test strip 100 also includes a distal portion 3 and a proximal portion 4 as shown in FIGS. 1 and 2.

Figure 2:
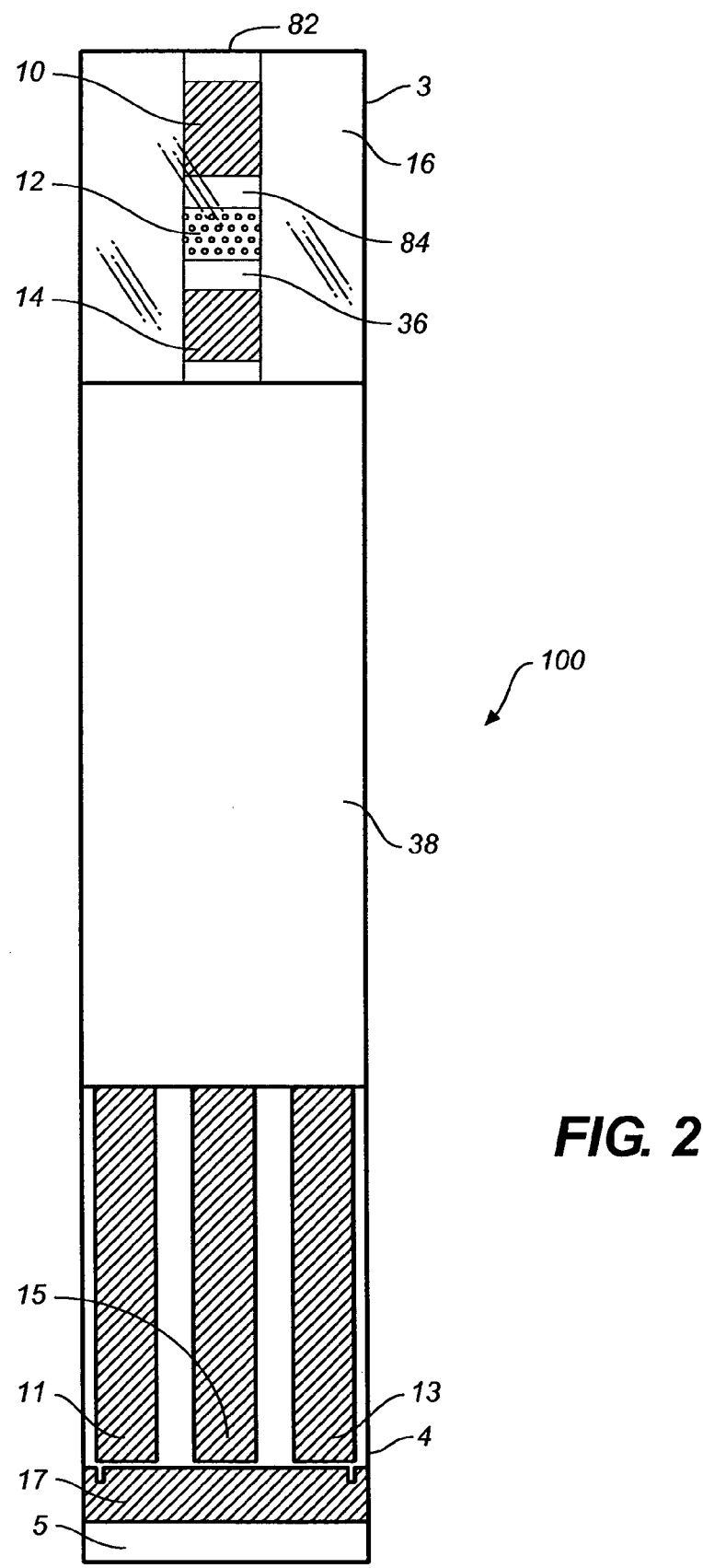
FIG. 2 is a top view of the test strip as shown in FIG. 1 after it has been assembled.
Figure 12:
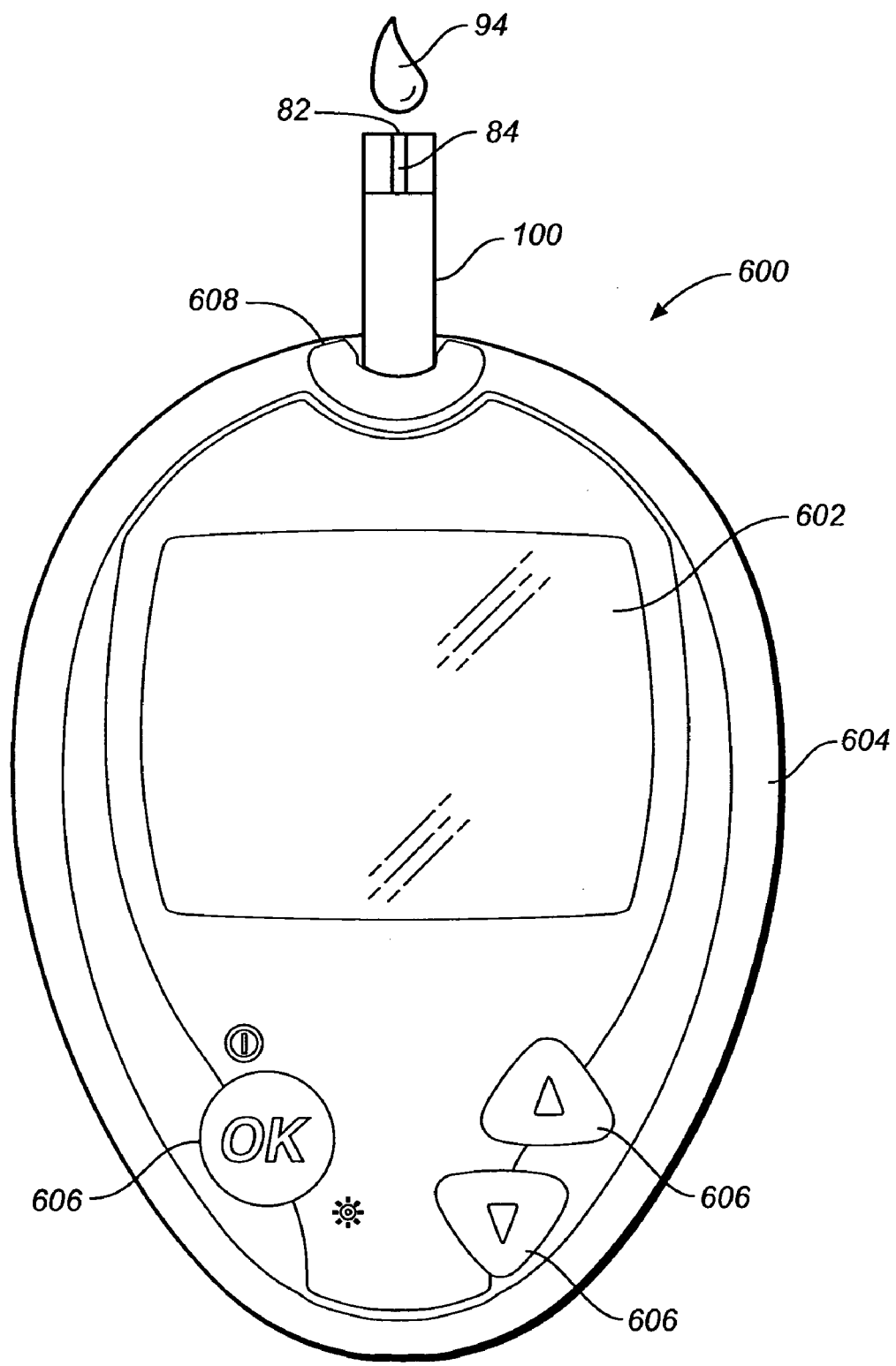
FIG. 12 is a top view of a test meter connected to the test strip of FIGS. 1 and 2.

The fully assembled test strip 100, as shown in FIG. 2, includes an inlet 82 through which a blood sample may be drawn into a sample receiving chamber 84. Inlet 82 may be formed by cutting through a distal portion 3 of test strip 100. A blood sample 94 can be applied to inlet 82 to fill a sample receiving chamber 84 so that glucose can be measured, as shown in FIG. 12. The side edges of a first adhesive pad 24 and a second adhesive pad 26 located adjacent to reagent layer 22 each define a wall of sample receiving chamber 84. A bottom portion or "floor" of sample receiving chamber 84 includes a portion of substrate 5, conductive layer 50, and insulation layer 16. A top portion or "roof" of sample receiving chamber 84 includes distal hydrophilic portion 32.

For test strip 100, as shown in FIG. 1, conductive layer 50 includes a reference electrode 10, a first working electrode 12, a second working electrode 14, a first contact 13, a second contact 15, a reference contact 11, and a strip detection bar 17. Suitable materials which may be used for the conductive layer are Au, Pd, Ir, Pt, Rh, stainless steel, doped tin oxide, carbon, and the like. In one embodiment, the material for the conductive layer may be a carbon ink such as those described in U.S. Pat. No. 5,653,918. In another embodiment, the material for the conductive layer may be a sputtered metal such as gold or palladium. A laser ablated pattern may be formed into the sputtered metal layer to form a plurality of electrodes.

For test strip 100, insulation layer 16 includes first aperture 18 which exposes a portion of reference electrode 10, openings 20 which expose a portion of first working electrode 12, and second aperture 21 which exposes a portion of second working electrode 14. The portions of reference electrode 10, first working electrode 12 and second working electrode 14 exposed by first aperture 18, openings 20 and second aperture 21, respectively, can be wetted by a liquid sample as shown in FIG. 1. Openings 20 in insulation layer expose a plurality of microelectrodes 120 as will be described with reference to FIGS. 5-9. In one exemplary embodiment, insulation layer 16 is Ercon E6110-116 Jet Black Insulayer™ ink that may be purchased from Ercon, Inc (Waltham, Mass.).

Reagent layer 22 may be disposed on a portion of conductive layer 50, substrate 5, and insulation layer 16 as shown in FIG. 1. In an embodiment, reagent layer 22 may include an enzyme, a mediator that selectivity reacts with glucose and a buffer for maintaining a desired pH. Examples of enzymes suitable for use in this invention may include either glucose oxidase or glucose dehydrogenase. More specifically, the glucose dehydrogenase may have a pyrroloquinoline quinone co-factor (abbreviated as PQQ or may be referred to its common name which is methoxatin). Examples of mediator suitable for use in this invention may include either ferricyanide or ruthenium hexamine ($Ru^{III}(NH_3)_6$). During the reactions as shown in Equations 1 and 2, a proportional amount of reduced mediator can be generated that is electrochemically measured for calculating a glucose concentration. Examples of buffers suitable for use in the present invention may include phosphate, citrate or citraconate. Examples of reagent formulations or inks suitable for use in the present invention can be found in U.S. Pat. Nos. 5,708,247 and 6,046,051 and published international applications WO01/67099 and WO01/73124.

In an embodiment, the formulation may include a 200 millimolar phosphate buffer having a pH of about 7 and a ruthenium hexamine mediator. The pH of around 7 was chosen because glucose oxidase has a sufficiently high activity at this pH when using ruthenium hexamine as a mediator. In an embodiment, the formulation may have an enzyme activity ranging from about 1500 units/mL to about 8000 units/mL. The enzyme activity range may be selected so that the glucose current does not depend on the level of enzyme activity in the formulation so long as the enzyme activity level is within the above stated range. The enzyme activity should be sufficiently large to ensure that the resulting glucose current will not be dependent on small variations in the enzyme activity. For instance, the glucose current will depend on the amount of enzyme activity in the formulation if the enzyme activity is less than 1500 units/mL. On the other hand, for enzyme activity levels greater than 8000 units/mL, solubility issues may arise where the glucose oxidase cannot be sufficiently dissolved in the formulation. Glucose oxidase may be commercially available from Biozyme Laboratories International Limited (San Diego, Calif., U.S.A.). The glucose oxidase may have an enzyme activity of about 250 units/mg where the enzyme activity units are based on an o-dianisidine assay at pH 7 and 25° C.

Optionally, reagent layer 22 includes a matrix material that aides in retaining the reagent layer 22 on the surface of conductive layer 50 in the presence of fluid sample. Useful matrix materials include silicas such as Cab-o-Sil® TS630 or Cab-o-Sil® 530 (Cabot Corporation, Boston, USA). While not wishing to be bound by any particular theory, it is believed that silica forms a gel network in the presence of the sample that effectively maintains the coating on the surface of the electrode. Other useful matrix materials include polymeric materials such as polyethersulfones, acrylic and methacrylic acid polymers; polymers derived from starch, cellulose and other natural polysaccharides; polyamides and collagen. An example of a useful coating composition is disclosed in Example 1 of U.S. Pat. No. 5,708,247. Reagent layer 22 may also optionally include at least one stabilizing agent such as albumin, sucrose, trehalose, mannitol or lactose, an agent such as hydroxyethylcellulose to adjust the viscosity, an anti-foam agent such as DC1500, and at least one wetting agent such as polyvinylpyrrilidone or polyvinyl acetate.

For test strip 100, adhesive layer 60 includes first adhesive pad 24, second adhesive pad 26, and third adhesive pad 28 as shown in FIG. 1. In an embodiment, adhesive layer 60 may comprise a water based acrylic copolymer pressure sensitive adhesive, which is commercially available from Tape Specialties LTD (Tring, Herts, United Kingdom; part#A6435). Adhesive layer 60 is disposed on a portion of insulation layer 16, conductive layer 50, and substrate 5. Adhesive layer 60 binds hydrophilic layer 70 to test strip 100.

Hydrophilic layer 70 includes a distal hydrophilic portion 32 and proximal hydrophilic portion 34. As a non-limiting example, hydrophilic layer 70 is a polyester having one hydrophilic surface such as an anti-fog coating which is commercially available from 3M.

For test strip 100, top layer 80 includes a clear portion 36 and opaque portion 38 as shown in FIG. 1. Top layer 80 is disposed on and adhered to hydrophilic layer 70. In one embodiment, top layer 80 is a polyester. It should be noted that the clear portion 36 substantially overlaps distal hydrophilic portion 32 that allows a user to visually confirm that the sample receiving chamber 84 is sufficiently filled. Opaque portion 38 helps the user observe a high degree of contrast between a colored fluid such as, for example, blood within the sample receiving chamber 84 and the opaque portion 38 of top layer 80.

Figure 3:
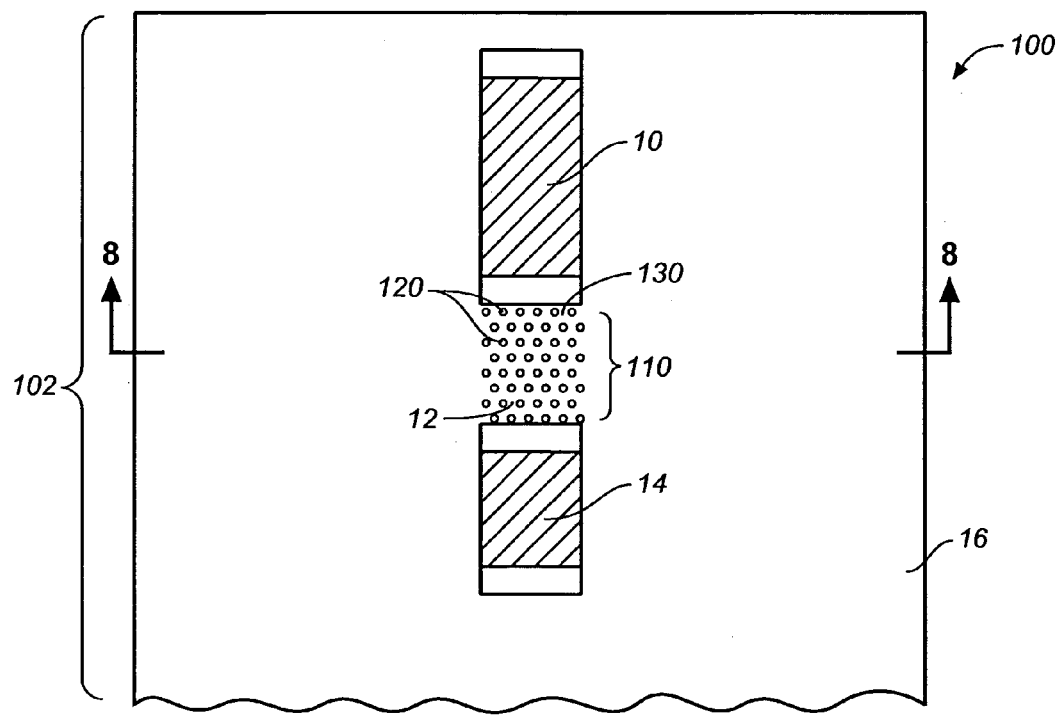
FIGS. 3-7 are top views of a distal portion of a partially assembled test strip according to exemplary embodiments of the present invention.

FIG. 3 shows a simplified top view of a partial assembly of a test strip 100 that includes a first working electrode 12 in the form of a microelectrode array 110 according to an exemplary embodiment. In general, microelectrode array 110 will enhance the effects of radial diffusion causing an increase in the measured current density (current per unit area of the working electrode). Radial diffusion refers to the flux of reduced mediator that diffuses to first working electrode 106 in a non-perpendicular manner with respect to a plane of first working electrode 106. In contrast, planar diffusion refers to the flux of reduced mediator that diffuses to first working electrode 106 in an approximately perpendicular manner with respect to a plane of first working electrode 106. As a result of the enhanced radial diffusion, the application of a limiting test voltage to microelectrode array 110 can cause a test current to achieve a non-zero steady-state value that is independent of time. In contrast, the application of a limiting test voltage to a non-microelectrode will result in a test current that approaches zero as time progresses. Because the steady-state value is independent of time for a microelectrode array 110, an effective diffusion coefficient D of the mediator in the blood sample may be calculated. In turn, effective diffusion coefficient D can be used as an input into an algorithm for reducing the effects of hematocrit.

Referring again to FIG. 3, a distal portion 102 of test strip 100 includes a reference electrode 10, a first working electrode 12 and a second working electrode 14. First working electrode 10 is in the form of a microelectrode array 110 that includes a plurality of microelectrodes 120.

Figure 4:
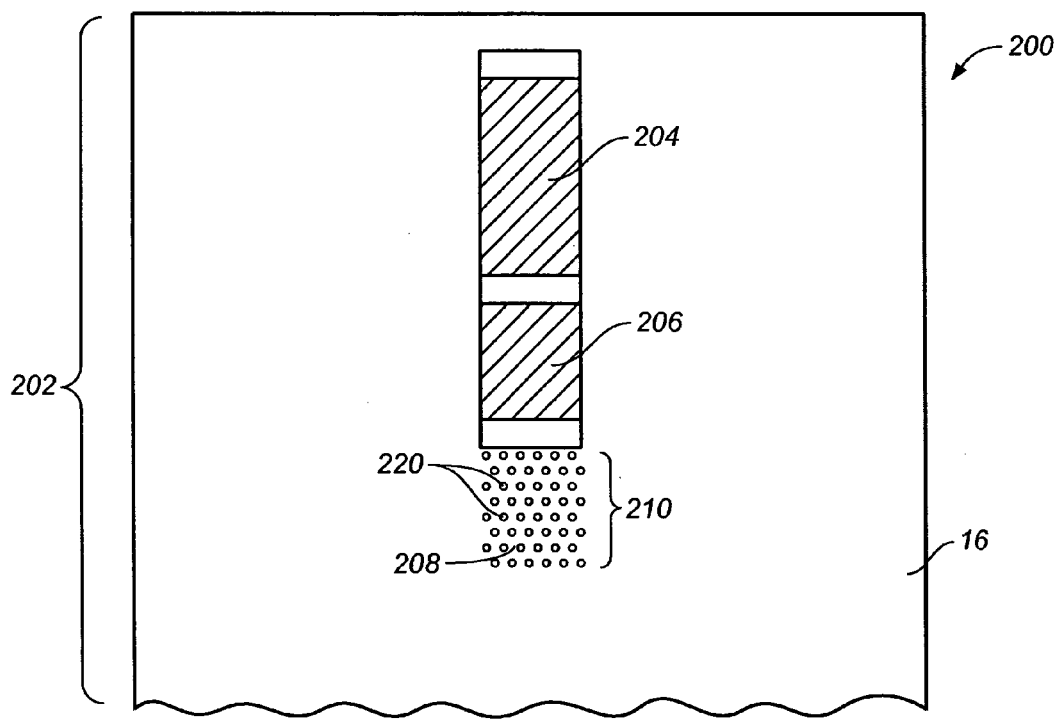
Figure 5:
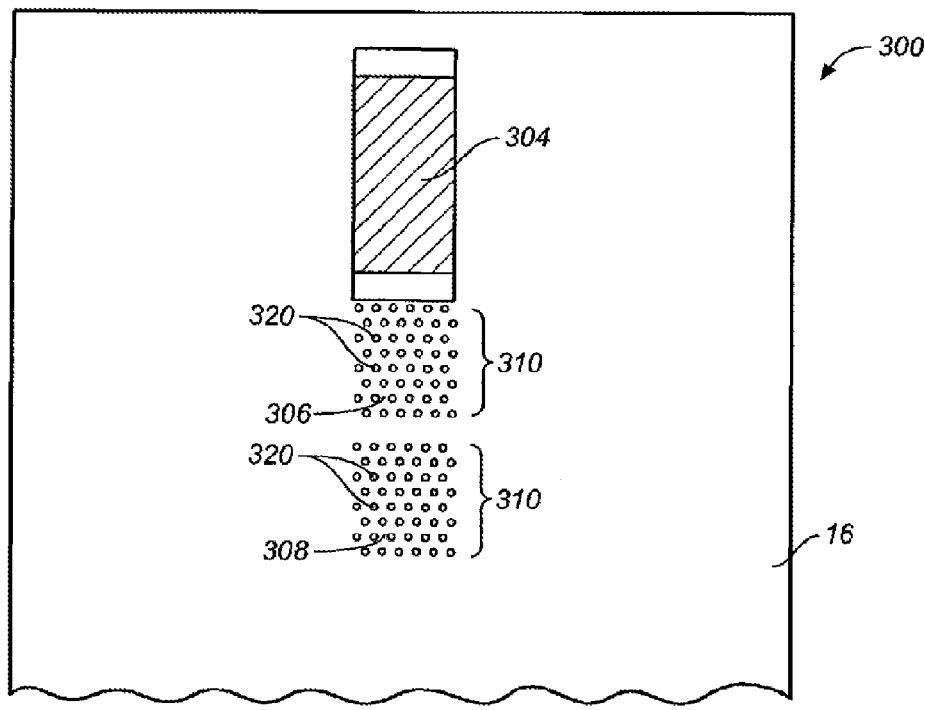

In another embodiment shown in FIG. 4, a distal portion 202 of a test strip 200 includes a reference electrode 204, a first working electrode 206 and a second working electrode 208. Test strip 200 differs from test strip 100 in that a second working electrode 208 includes a microelectrode array 210 with a plurality of microelectrodes 220. In yet another embodiment shown in FIG. 5, both a first working electrode 306 and a second working electrode 308 include a microelectrode array 310 with a plurality of microelectrodes 320.

Figure 6:
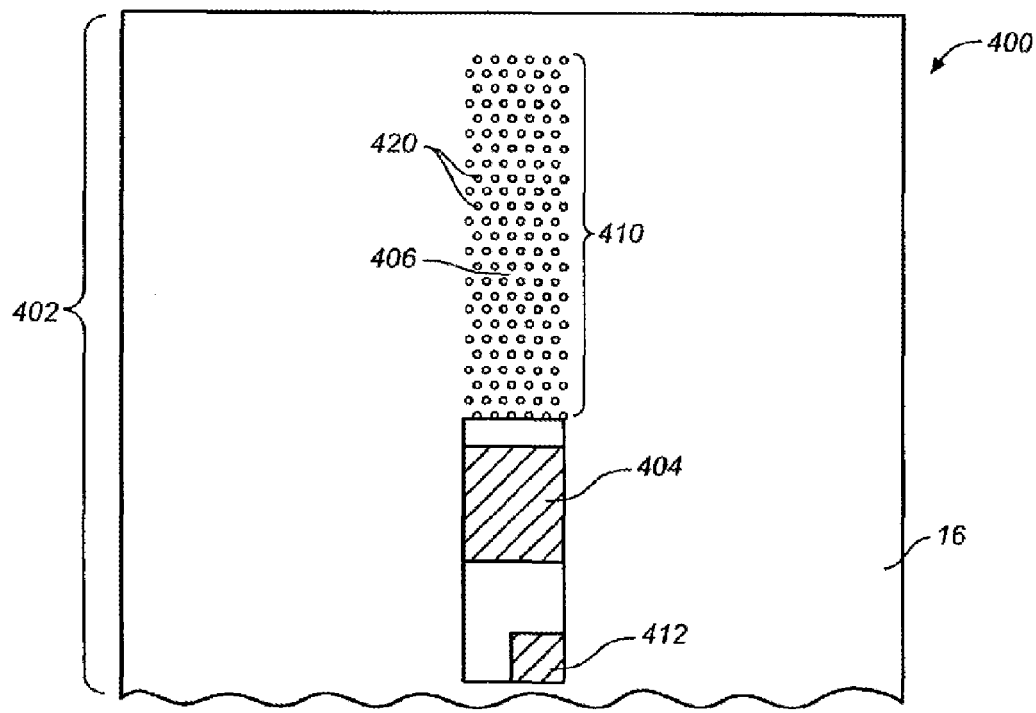

Another embodiment of a test strip 400 having a microelectrode array 410 is shown in FIG. 6. A distal portion 402 of test strip 400 includes a reference electrode 404, a working electrode 406 and a fill detect electrode 412. Working electrode 406 is in the form of a microelectrode array 410 that includes a plurality of microelectrodes 420. Test strip 400 differs from test strip 100 in that working electrode 406 is located upstream of reference electrode 404 and does not include a second working electrode. As shown in FIG. 6, working electrode 406 may optionally be at least twice the surface area of reference electrode 404.

Figure 7:
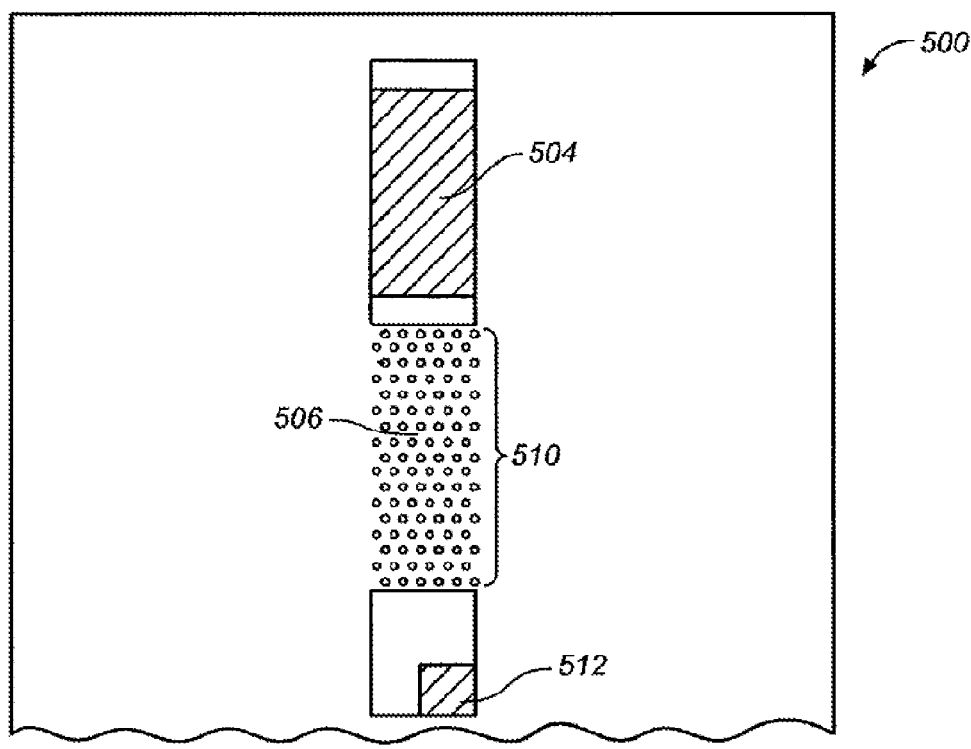

FIG. 7 shows yet another embodiment of a test strip 500 in which test strip 500 includes a reference electrode 504 and a working electrode 506. In this embodiment, reference electrode 504 and working electrode 506 are of approximately equal surface area. Working electrode 506 includes a microelectrode array 510 and is downstream from reference electrode 504 with respect to fluid flow in test strip 500. FIG. 7 also shows an optional fill detect electrode 512.

Many of the layers of test strip 100, as shown in FIG. 1, may be used for test strips 100, 200, 300, 400 and 500, such as insulation layer 16, reagent layer 22, adhesive layer 60, hydrophilic layer 70, and top layer 80.

Figure 8:
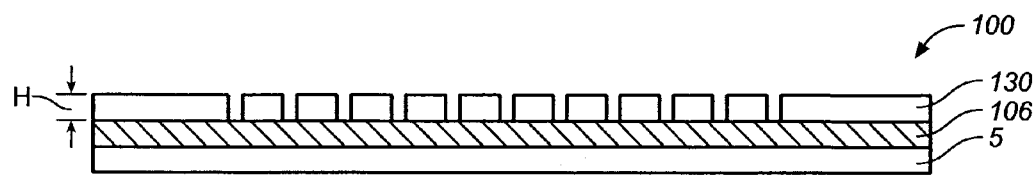
FIG. 8 is a cross sectional view of the test strip shown in FIG. 3 through a microelectrode array on a first working electrode according to an exemplary embodiment.

FIG. 8 is a cross-sectional view through microelectrode array 110 on first working electrode 106 of FIG. 3 showing that an insulation portion 130 is disposed on first working electrode 106. In one exemplary embodiment, insulation portion 130 is contiguous with insulation layer 16 of FIG. 1. Thus, in this embodiment, insulation portion 130 is printed in the same step as the printing of insulation layer 16. Laser ablating insulation portion 130 to form openings 20 which expose a plurality of microelectrodes 120 may then form microelectrode array 110.

In another embodiment, insulation portion 130 is a separate element from insulation layer 16 of FIG. 1. In this embodiment, insulation portion 130 is disposed on first working electrode 106 in a step separate from the printing of insulation layer 16. Insulation portion 130 may be disposed over and bound to first working electrode 106 by processes such as ultrasonic welding, screen-printing, or through the use of an adhesive. In this embodiment, openings 20 in insulation portion 130 may be formed before or after adhering insulation portion 130 to first working electrode 106.

Figure 9:
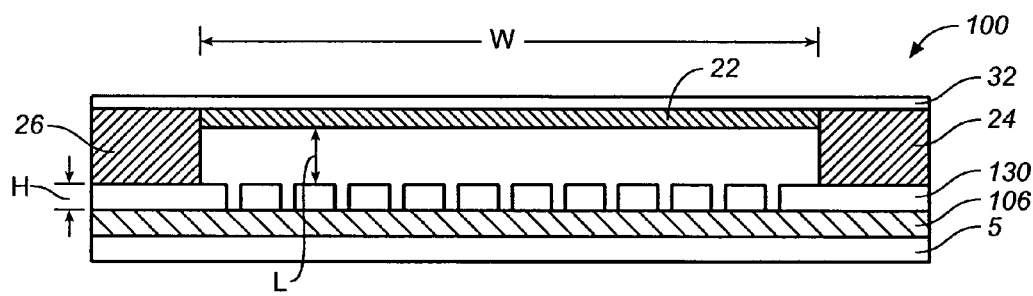
FIG. 9 is a cross sectional view through a microelectrode array on a first working electrode of FIG. 3 with additional layers coated on an insulation portion including a reagent layer, adhesive pads, and a hydrophilic portion. The reagent layer is disposed on the distal side of the hydrophilic portion according to an exemplary embodiment.
Figure 10:
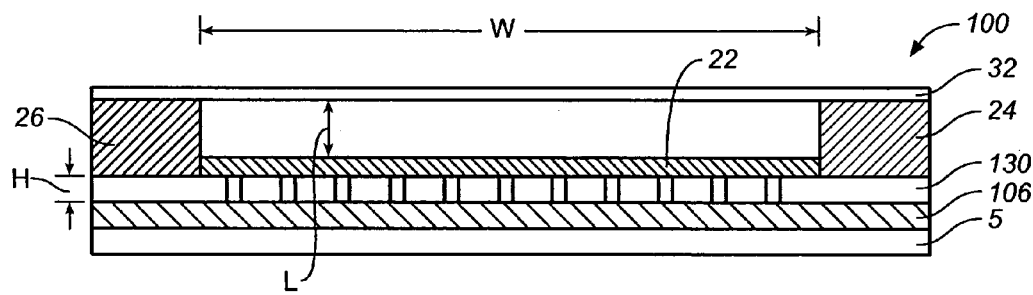
FIG. 10 is a cross sectional view through a microelectrode array on a first working electrode of FIG. 3 with additional layers coated on an insulation portion including a reagent layer, adhesive pads, and a hydrophilic portion. The reagent layer is disposed over the insulation portion according to an exemplary embodiment.

FIGS. 9 and 10 are cross-sectional views through microelectrode array 110 on first working electrode 106 of FIG. 3 with additional layers including reagent layer 22, adhesive pads 24 and 26, and hydrophilic portion 32. Reagent layer 22 may be disposed on distal hydrophilic portion 32 as shown in FIG. 9. In this embodiment, reagent layer 22 is highly soluble, ensuring that when a fluid sample is applied to test strip 100, reagent layer 22 readily dissolves and the mediator quickly diffuses to microelectrodes 120. Alternatively, reagent layer 22 may be disposed over an insulation portion 130 as shown in FIG. 10. In this embodiment, reagent layer 22 may be insoluble because of the close proximity of reagent layer 22 to microelectrodes 120. First and second adhesive pads 24 and 26 are applied in such a manner as to define a gap height L between insulator portion 130 and reagent layer 22 (see FIG. 9) or between reagent layer 22 and distal hydrophilic portion (see FIG. 10). First and second adhesive pads 24 and 26 also define a width W of reagent layer 22.

For microelectrode array 110 to have an enhanced effect due to radial diffusion, insulation portion 130 should have the appropriate dimensions. In one aspect, insulation portion 130 may include a height H that is between about 1 microns and about 6 microns. It is necessary that insulation portion 130 be sufficiently thin so as to allow radial diffusion. If insulation portion 130 is much greater than 6 microns, then insulation portion 130 interferes with radial diffusion and would actually promote planar diffusion.

Figure 11:
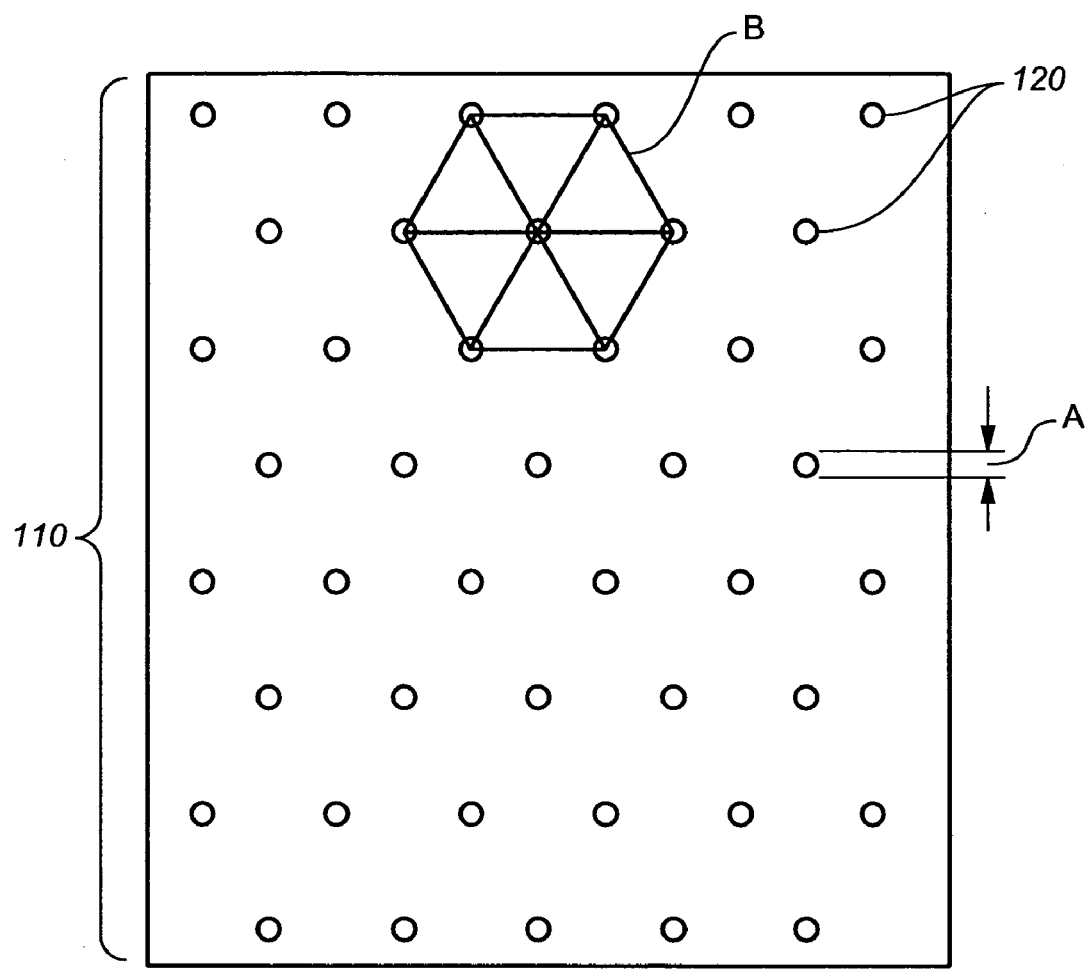
FIG. 11 is a top, close up view of the plurality of microelectrodes on the first working electrode of the test strip shown in FIG. 3 according to an exemplary embodiment.

In another aspect shown in FIG. 11, each microelectrode 120 should be spaced sufficiently far from each other so as to prevent a first microelectrode from competing with an adjacent second microelectrode for oxidizing mediator. Each microelectrode 120 may be spaced apart with a distance B ranging from about 5 times to about 10 times the diameter of microelectrode 120. In one embodiment as shown in FIG. 10, each microelectrode 120 may be evenly spaced throughout insulation portion 130, where a microelectrode may have six neighboring microelectrodes which form a hexagonal shape.

In yet another aspect, each microelectrode 120 should be sufficiently small such that the proportion of the test current ascribed to radial diffusion is greater than the proportion of the test current ascribed to planar diffusion. Microelectrode 120 may have a disk shape with a diameter A ranging from about 3 microns to about 20 microns. In alternative embodiments, microelectrode 120 may be square, rectangular, elliptical or oval in shape.

In another aspect, microelectrode array 110 may be any geometric shape including, but not limited to, a circle, an oval, a square or a rectangle. If rectangular in shape, the surface area is generally between about 0.3 and about 3 square microns.

FIG. 12 illustrates a test meter 600 suitable for connecting to test strip 100. Test meter 600 includes a display 602, a housing 604, a plurality of user interface buttons 606, and a strip port connector 608. Test meter 600 further includes electronic circuitry within housing 604 such as a memory, a microprocessor, electronic components for applying a test voltage, and also for measuring a plurality of test current values. Proximal portion 4 of test strip 100 may be inserted into strip port connector 608. Display 102 may output a glucose concentration and be used to show a user interface for prompting a user on how to perform a test. The plurality of user interface buttons 606 allow a user to operate test meter 600 by navigating through the user interface software.

Figure 13:
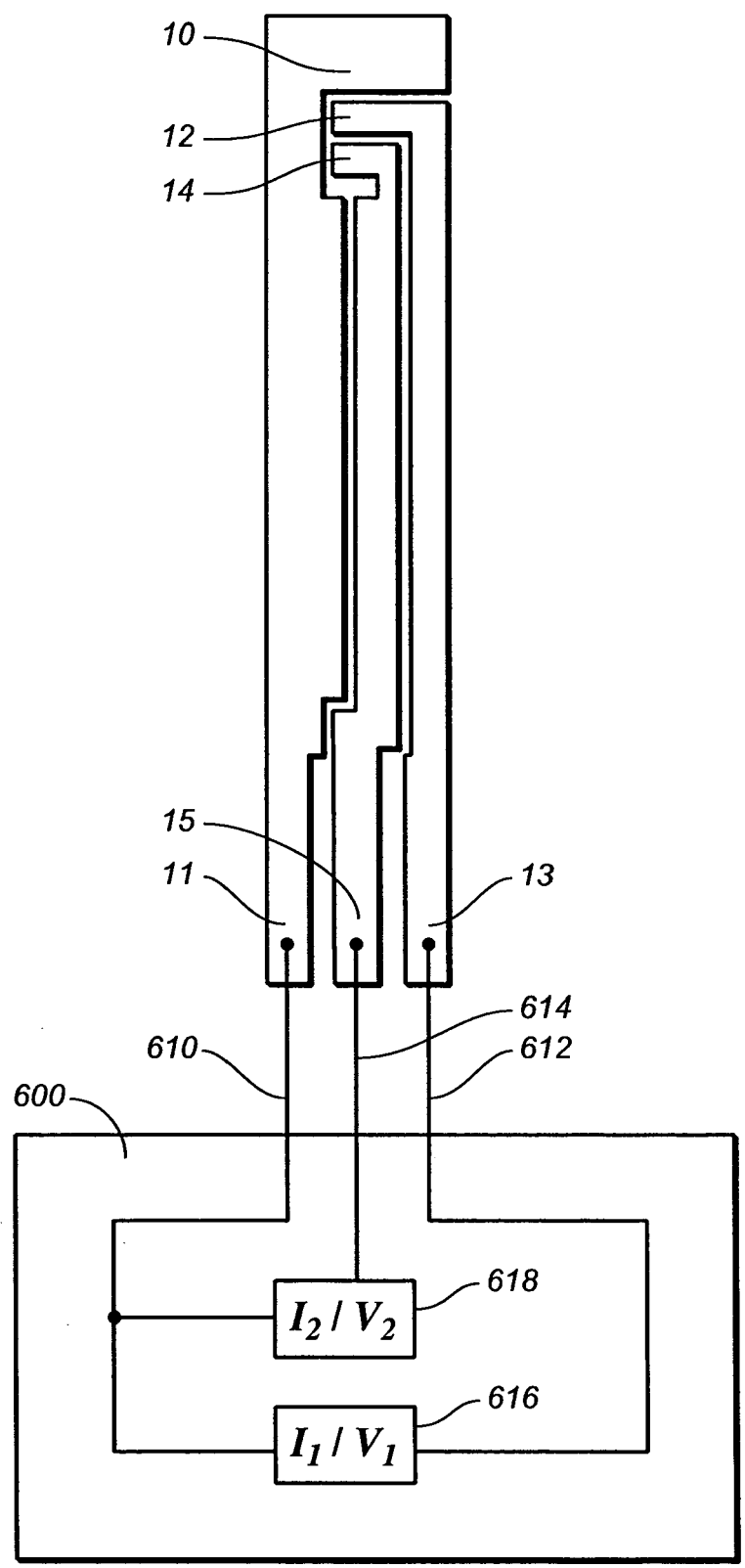
FIG. 13 is a simplified schematic view of the test meter of FIG. 12 forming an electrical connection with the test strip of FIGS. 1 and 2.

FIG. 13 shows a simplified schematic of a test meter 600 interfacing with test strip 100. Test meter 600 includes a first connector 612, second connector 614, and a reference connector 610 which respectively form an electrical connection to first contact 13, second contact 15, and reference contact 11. The three aforementioned connectors are part of strip port connector 608. When performing a test, a first test voltage source 616 may apply a first test voltage $V_1$ between first working electrode 12 and reference electrode 10. As a result of first test voltage $V_1$, test meter 600 may then measure a first test current $I_1$. In a similar manner, second test voltage source 618 applies a second test voltage $V_2$ between second working electrode 14 and reference electrode 10. As a result of second test voltage $V_2$, test meter 600 may then measure a second test current $I_2$. In an embodiment, first test voltage $V_1$ and second test voltage $V_2$ may be about equal allowing a glucose measurement to be performed twice where a first measurement is performed with first working electrode 12 and a second measurement is performed with second working electrode 14. The use of two glucose measurements can increase accuracy by averaging the two results together. For simplifying the description of the following sections, the algorithms for determining a hematocrit corrected glucose concentration will be described for only one working electrode and reference electrode. It should be apparent to one skilled in the art that the invention should not be limited to one working electrode and reference electrode, but that multiple working electrodes may also be applied to the present invention.

The following methods will describe algorithms that may be applied to microelectrodes and, more particularly, to microelectrode arrays, where the test current achieves a steady-state value because of a higher proportion of radial diffusion.

FIG. 18 is a flowchart illustrating a sequence of steps in a method 700 used by test meter 600 to apply a hematocrit correction to a glucose concentration according to an exemplary embodiment.

Method 700 includes providing a test strip 100 with a reference electrode 10, a first working electrode 12, an optional second electrode 14 and a test meter 600, as set forth by step 710. First working electrode 12 includes a plurality of microelectrodes 120 (i.e., microelectrode array 110) with each disk shaped microelectrode having a diameter of about 3 microns to about 50 microns and separated by about 5 to about 10 times the diameter thereof. Reference electrode 10 includes a surface area that is at least equal to the surface area of microelectrode array 110.

Figure 14:
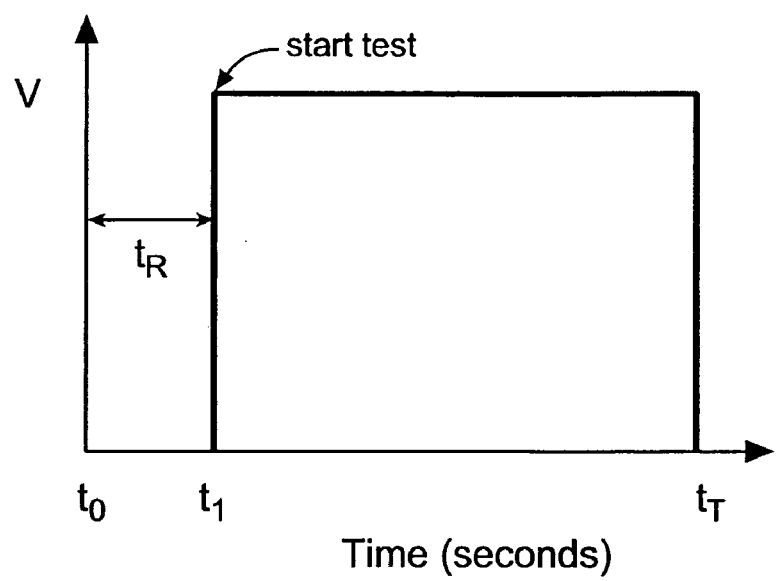
FIGS. 14 and 15 are graphical representations of a test voltage applied to a working electrode of a test strip according to methods of the present invention.
Figure 15:
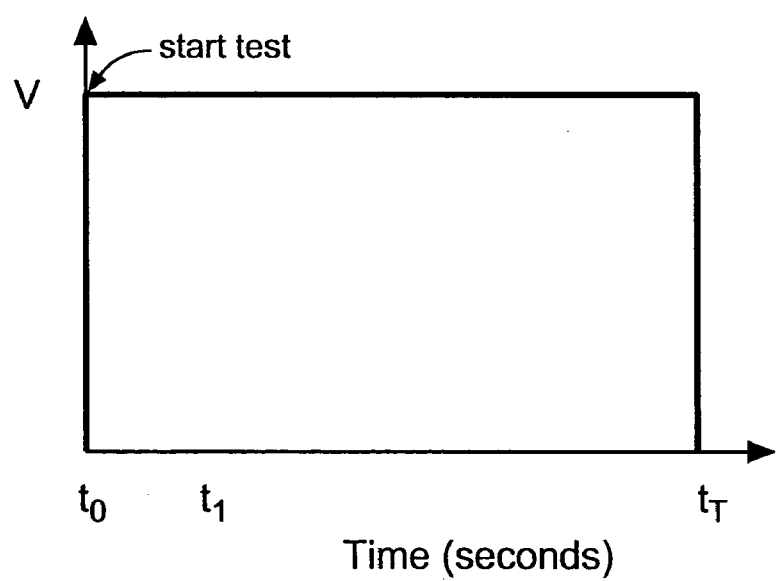

FIG. 14 is a graphical representation of a test voltage applied to test strip 100 according to the method. Before a fluid sample is applied to test strip 100, test meter 600 is in a fluid detection mode in which a test voltage (not shown) of about 100 millivolts to about 600 millivolts, typically 400 millivolts is applied between first working electrode 12 and reference electrode 10. As set forth in step 720, the fluid sample is applied to test strip 100 at $t_0$ and is allowed to react with reagent layer 22 for a reaction period $t_R$. The presence of sample in the reaction zone of test strip 100 is determined by measuring the current flowing through first working electrode 12. The beginning of reaction period $t_R$ is determined to begin when the current flowing through first working electrode 12 reaches a desired value, typically about 0.150 nanoamperes (not shown), at which point a test voltage of zero millivolts is applied between first working electrode 12 and reference electrode 10. Reaction period $t_R$ is typically between about 2 and about 3 seconds and is more typically about 2.5 seconds. After reaction period $t_R$, the test voltage in the exemplary method is applied to test strip 100 at $t_1$ for a total test time $t_T$. In an alternative method shown in FIG. 15, the reaction period $t_R$ is omitted such that the start of the test commences as soon as sufficient current is flowing through first working electrode 12.

Figure 16:
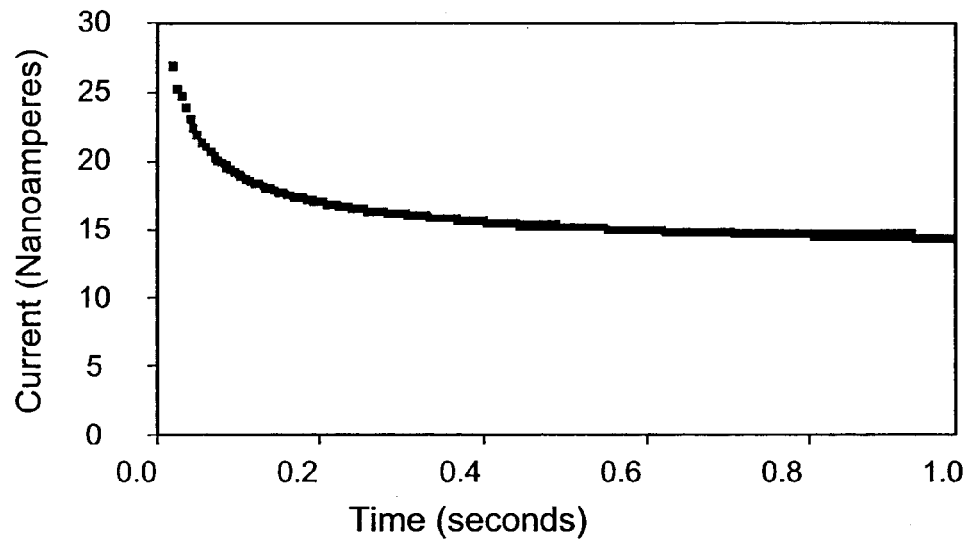
FIG. 16 is a plot of current as a function of time (i.e., a current-time transient) for a fluid sample which is generated by a method.

As set forth in step 730, a limiting test voltage of about 100 millivolts to about 600 millivolts, typically 400 millivolts, is applied between reference electrode 10 and first working electrode 12 and a test current is measured as a function of time, as illustrated in FIG. 16. Note that the test current approaches a steady-state current value as time progresses. A steady state current value $I_{SS}$ is measured when an equilibrium current value is attained, as set forth by step 740. Steady state current value $I_{SS}$ generally is reached between about 0.5 and about 2 seconds after the test voltage is applied to test strip 100.

As set forth in step 750, the ratio of the test current to a steady state current value $$\frac{I(t)}{I_{ss}}$$

is then calculated for each time point at which test current is measured. For microelectrode array 110 having a plurality of disk-shaped microelectrodes 120 where a limiting test voltage is applied, the following equation estimates a ratio of the test current to the steady-state current value:

$$\frac{I(t)}{I_{ss}} = 1 + \left(\frac{2r_d}{\pi\sqrt{\pi Dt}}\right) \quad (4)$$

Where:
I(t) is the test current in microamperes measured at time t;
$I_{SS}$ is the steady-state current value in microamperes;
$r_d$ is the radius of microelectrode 120 in centimeters;
t is time in seconds; and
D is the effective diffusion coefficient in units of centimeter$^2$/second.

The effective diffusion coefficient D takes into account the diffusion of the mediator in a blood sample having a dissolved reagent layer. In general, the effective diffusion coefficient D should decrease with increasing hematocrit levels. Thus, the effective diffusion coefficient D is dependent on the hematocrit level and can be used in an algorithm for decreasing the effects of hematocrit. The following will describe how to calculate the effective diffusion coefficient D and then apply the effective diffusion coefficient D for calculating a glucose concentration.

Figure 17:
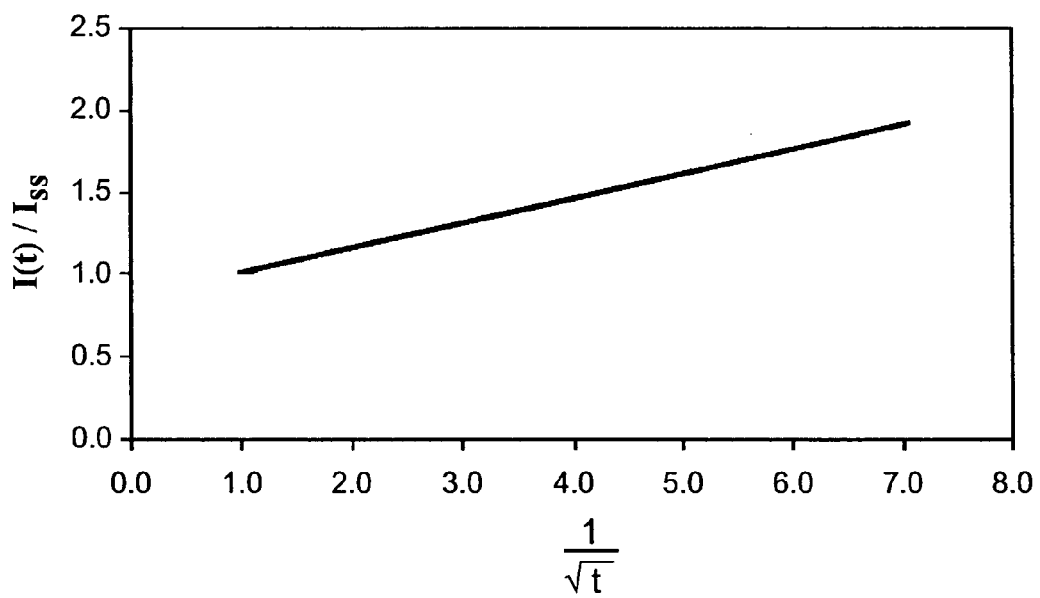
FIG. 17 is a plot of $$\frac{I(t)}{I_{ss}}$$

Using Equation 4, effective diffusion coefficient D may be calculated by plotting the values $$\frac{I(t)}{I_{ss}}$$

on the y-axis and $$\frac{1}{\sqrt{t}}$$

on the x-axis as illustrated in FIG. 17 and set forth in step 760. The resulting slope from the linear portion of the line may then be calculated and converted into effective diffusion coefficient D, as set forth in step 770. In practice, all the calculations required to determine effective diffusion coefficient D would be pre-programmed into the test meter as an algorithm. An advantage of this approach of determining effective diffusion coefficient D is that effective diffusion coefficient D is independent of glucose concentration.

As set forth in step 780, effective diffusion coefficient D may be used with Equation 5 below to estimate the reduced mediator concentration $C_{red}$ (e.g., concentration of $Fe(CN)_6^{4-}$).

$$C_{red} = \frac{I_{ss}}{4nFDr_d} \quad (5)$$

Where:

n is the number of electrons exchanged per reduced mediator molecule;

F is Faraday's constant.

$C_{red}$ can then be used to estimate the hematocrit-corrected glucose concentration. For example, a calibration curve may be generated in which the y-axis is $C_{red}$ where $C_{red}$ is calculated for whole blood samples with a range of glucose and hematocrit concentrations. The x-axis is the reference glucose concentration $G_{ref}$ of the same whole blood samples as measured on a reference glucose analyzer. The calibration intercept may be subtracted from $C_{red}$ followed by a division using a calibration slope to yield glucose concentration $G_{ref}$. In summary, Equations 1 and 2 allow for glucose concentrations to be calculated with a reduced effect from hematocrit when using microelectrode arrays as illustrated in FIGS. 3 to 7, thus resulting in a more accurate glucose concentration.

Lastly, the hematocrit-corrected analyte concentration is displayed on test meter 600, as set forth in step 790.

FIG. 19 is a flowchart illustrating a sequence of steps in a method 800 used by test meter 600 to establish whether a fluid sample is a bodily fluid (e.g., whole blood) or a control solution according to an exemplary embodiment. A control solution is used to ensure that the test meter and test strip are functioning properly. In one embodiment, analyte concentrations for a bodily fluid are averaged over a period of time to assess the patient's health. If a control solution value is stored in the test meter as an analyte concentration, the average analyte concentration for bodily fluid will be incorrect. Thus, having a method to distinguish between a bodily fluid and a control solution is advantageous.

Method 800 includes providing a test strip 100 with a reference electrode 10, a first working electrode 12, an optional second electrode 14 and a test meter 600, as set forth by step 810. First working electrode 12 includes a plurality of microelectrodes 120 (i.e., microelectrode array 110) with each disk shaped microelectrode having a diameter of about 3 to about 50 microns and separated by about 5 to about 10 times the diameter thereof. Reference electrode 10 includes a surface area that is at least equal to the surface area of microelectrode array 110.

As set forth in step 820, the fluid sample is applied to test strip 100 at $t_o$ and is allowed to react with reagent layer 22 for a reaction period $t_R$ (see FIG. 14). The presence of sample in the reaction zone of test strip 100 is determined by measuring the current flowing through first working electrode 12. The beginning of reaction period $t_R$ is determined to begin when the current flowing through first working electrode 12 reaches a desired value, typically about 0.150 nanoamperes (not shown), at which point a test voltage of between about −50 millivolts and about +50 millivolts, typically about zero millivolts, is applied between first working electrode 12 and reference electrode 10. Reaction period $t_R$ is typically between about 2 and about 3 seconds and is more typically about 2.5 seconds. After reaction period $t_R$, the test voltage in the exemplary method is applied to test strip 100 at $t_i$ for a total test time $t_T$. In an alternative method shown in FIG. 15, the reaction period $t_R$ is omitted such that the start of the test commences as soon as sufficient current is flowing through first working electrode 12.

As set forth in step 830, a limiting test voltage of about 100 millivolts to about 600 millivolts, typically 400 millivolts, is applied between reference electrode 10 and first working electrode 12 and test current is measured as a function of time, as illustrated in FIG. 16. A steady state current value $I_{SS}$ is measured when an equilibrium current value is attained, as set forth by step 840. Steady state current value $I_{SS}$ generally is reached between about 0.5 and about 2 seconds after the test voltage is applied to test strip 100.

As set forth in step 850, the ratio of the test current to a steady state current value $$\frac{I(t)}{I_{ss}}$$

is then calculated for each time point at which test current is measured. For microelectrode array 110 having a plurality of disk-shaped microelectrodes 120 where a limiting test voltage is applied, Equation 4 above is used to estimate a ratio of the test current to the steady-state current value.

Using Equation 4, effective diffusion coefficient D may also be calculated by plotting the values $$\frac{I(t)}{I_{ss}}$$

on the y-axis and $$\frac{1}{\sqrt{t}}$$

on the x-axis as illustrated in FIG. 17 and set forth in step 860. The resulting slope from the linear portion of the line may then be calculated and converted into effective diffusion coefficient D, as set forth in step 870.

As set forth in step 880, effective diffusion coefficient D may be used with Equation 5 above to estimate the reduced mediator concentration $C_{red}$ (e.g., concentration of $Fe(CN)_6^{4-}$).

To determine the type of fluid sample (e.g., bodily fluid or control solution) applied to test strip 100, test meter 600 compares a measured value for effective diffusion coefficient D to an acceptance range for bodily fluid and an acceptance range for control solution, as set forth by step 880. For whole blood having a hematocrit level between about 20% and about 70%, effective diffusion coefficient D is typically between about $0.7 \times 10^{-6}$ centimeters$^2$/second and about $2.7 \times 10^{-6}$ centimeters$^2$/second. Effective diffusion coefficient D for control solution typically is between about $4.0 \times 10^{-6}$ centimeters$^2$/second and about $7.2 \times 10^{-6}$ centimeters$^2$/second.

Finally, test meter 600 displays an appropriate error message if the fluid sample is not in the acceptance range for bodily fluid or control solution, depending on which type of fluid sample has been applied to test strip 100, or allows the user to proceed with testing, as set forth by step 890.

Estimated effective diffusion coefficient D can also be used to distinguish between test strips 100 that include microelectrodes 120 and those that do not include microelectrodes 120. Estimated effective diffusion coefficient d may also be used to determine if reagent layer 22 has been formulated or coated incorrectly. FIG. 20 is a flowchart illustrating a sequence of steps in a method 900 used by a test meter to determine if a test strip 100 includes a plurality of microelectrodes 120 and includes a reagent layer 22 that has been correctly formulated and coated according to an exemplary embodiment.

Method 900 includes providing a test strip 100 with a reference electrode 10, a first working electrode 12, an optional second electrode 14 and a test meter 600, as set forth by step 910. First working electrode 12 includes a plurality of microelectrodes 120 (i.e., a microelectrode array 110) with each microelectrode 120 having a diameter between about 3 microns and about 50 microns and separated by about 5 to about 10 times the diameter thereof. Reference electrode 10 includes a surface area that is at least equal to the surface area of microelectrode array 110.

As set forth in step 920, the fluid sample is applied to test strip 100 at $t_0$ and is allowed to react with reagent layer 22 for a reaction period $t_R$ (see FIG. 14). The presence of sample in the reaction zone of test strip 100 is determined by measuring the current flowing through first working electrode 12. The beginning of reaction period $t_R$ is determined to begin when the current flowing through first working electrode 12 reaches a desired value, typically about 0.150 nanoamperes (not shown), at which point a test voltage of zero millivolts is applied between first working electrode 12 and reference electrode 10. Reaction period $t_R$ is typically between about 2 and about 3 seconds and is more typically about 2.5 seconds. After reaction period $t_R$, the test voltage in the exemplary method is applied to test strip 100 at $t_1$ for a total test time $t_T$. In an alternative method shown in FIG. 15, the reaction period $t_R$ is omitted such that the start of the test commences as soon as sufficient current is flowing through first working electrode 12.

As set forth in step 930, a limiting test voltage of about 100 millivolts to about 600 millivolts, typically 400 millivolts, is applied between reference electrode 10 and first working electrode 12 and test current is measured as a function of time, as illustrated in FIG. 16. A steady state current value $I_{SS}$ is measured when an equilibrium current value is attained, as set forth by step 940. Steady state current value $I_{SS}$ generally is reached between about 0.5 and about 2 seconds after the test voltage is applied to test strip 100.

As set forth in step 950, the ratio of the test current to a steady state current value $$\frac{I(t)}{I_{SS}}$$

is then calculated for each time point at which the test current is measured. For microelectrode array 110 having a plurality of disk-shaped microelectrodes 120 where a limiting test voltage is applied, Equation 4 above is used to estimate a ratio of the test current to the steady-state current value.

Using Equation 4, effective diffusion coefficient D may be calculated by plotting the values $$\frac{I(t)}{I_{SS}}$$

on the y-axis and $$\frac{1}{\sqrt{t}}$$

on the x-axis as illustrated in FIG. 17 and set forth in step 960. The resulting slope from the linear portion of the line may then be calculated and converted into effective diffusion coefficient D, as set forth in step 970.

Next, as set forth by step 980, a temperature-corrected diffusion coefficient $\tilde{D}$ is calculated by substituting effective diffusion coefficient D into Equation 6 below that approximates the temperature-dependent diffusion in a gel.

$$\tilde{D} = D\exp\left\{\theta\left(\frac{1}{T} - \frac{1}{T_0}\right)\right\} \quad (6)$$

Where:
$\tilde{D}$ the temperature-corrected effective diffusion coefficient in centimeter$^2$/second;
D is the estimated effective diffusion coefficient in centimeter$^2$/second;
$\theta$ is a known constant for temperature-dependent diffusion;
T is temperature in Kelvin of the fluid sample as measured by the test meter and generally is between about 283° K and about 317° K; and
$T_0$ is a reference temperature (e.g., room temperature) in degrees Kelvin. $T_0$ ranges from about 293 degrees Kelvin to about 298 degrees Kelvin.

Next, test meter 600 determines if test strip 100 includes microelectrode array 110 and a correctly formulated and coated reagent layer 22 by comparing a calculated value of temperature-corrected effective diffusion coefficient $\tilde{D}$ against an acceptance range, as set forth by step 990. Temperature-corrected effective diffusion coefficient $\tilde{D}$ is typically about $1.8 \times 10^{-6}$ centimeters$^2$/second and usually is between about $1.6 \times 10^{-6}$ centimeters$^2$/second to $2.0 \times 10^{-6}$ centimeters$^2$/second.

Finally, if the calculated value for temperature-corrected effective diffusion coefficient $\tilde{D}$ is within the acceptance range, the user is allowed to proceed with testing. If, however, the calculated value for temperature-corrected effective diffusion coefficient $\tilde{D}$ is outside the acceptance range, test meter 600 displays an appropriate error message (e.g., the test strip was not recognized) to the user, as set forth by step 995.

FIG. 21 is a plot illustrating simulated values for temperature-corrected effective diffusion coefficient D̃ for test strips 100 that include microelectrode array 110 and those that do not include microelectrode array 110. Arrowhead M indicates an appropriate range of values for temperature-corrected effective diffusion coefficient D̃ for test strip 100 that include microelectrode array 110. Values for temperature-corrected effective diffusion coefficient D̃ of test strips that do not include microelectrode array 110 would lie outside of arrowhead M as indicated by arrowheads N1 and N2 on this plot.

FIGS. 22 and 23 are perspective and side views, respectively, of an integrated medical device 1000 that may include a plurality of microelectrodes 120 according to exemplary embodiments. Integrated medical device 1000 includes a test strip 1004 and a dermal tissue penetration member 1002. Test strip 1004 has a reaction area 1005 comprised of reagent layer 22 coated on reference electrode and one or more working electrodes (not shown). Electrical contacts 1006 terminate on a proximal end 1010 of integrated medical device 1000 and are formed of any suitable conductive material, such as gold, silver, platinum or carbon. Dermal tissue penetration member 1002 includes a lancet 1020 adapted to pierce a user's skin and draw blood into reaction area 1005. Dermal tissue penetration member 1002 is adhered to test strip 1004 by an adhesive layer 1014. This adhesive layer 1014 can be heat seal or pressure sensitive adhesive. Lancet 1020 includes a lancet base 1022 that terminates at the distal end 1012 of the assembled test strip. Further descriptions of integrated medical devices that may be used with the present invention are in the U.S. patent application Ser. No. 10/432,827 (published as 2004/0096959 on May 20, 2004) and U.S. patent application Ser. No. 10/143,399 (published as 2003/0143113 on Jul. 31, 2003).

While the invention has been described in terms of particular variations and illustrative figures, those of ordinary skill in the art will recognize that the invention is not limited to the variations or figures described. In addition, where methods and steps described above indicate certain events occurring in certain order, it is intended that certain steps do not have to be performed in the order described but in any order as long as the steps allow the embodiments to function for their intended purposes. Therefore, to the extent there are variations of the invention, which are within the spirit of the disclosure or equivalent to the inventions found in the claims, it is the intent that this patent will cover those variations as well.

What is claimed is:

1. A method of determining a type of fluid sample applied to the test strip, the method comprising:
providing a test strip having a reference electrode and a working electrode, wherein the working electrode is formed with a plurality of microelectrodes and is coated with a reagent layer;
applying a fluid sample to the test strip for a reaction period;
applying a test voltage between the reference electrode and the working electrode;
measuring a test current as a function of time;
measuring a steady state current value when the test current has reached an equilibrium;
calculating a ratio of the test current to the steady state current value;
plotting the ratio of the test current to the steady state current value as a function of the inverse square root of time;
calculating an effective diffusion coefficient from the slope of the linearly regressed plot of the ratio of the test current to the steady state current value as a function of the inverse square root of time;
determining a type of a fluid sample applied to the test strip by comparing a measured value for the effective diffusion coefficient against an acceptance range for a bodily fluid and a control solution; and
displaying an appropriate error message if the effective diffusion coefficient does not pass the acceptance range for the type of fluid sample applied to the test strip.

2. The method of claim 1, wherein the calculating of the effective diffusion coefficient step utilizes an equation of the form:

$$\frac{I(t)}{I_{SS}} = 1 + \left(\frac{2r_d}{\pi\sqrt{\pi Dt}}\right)$$

where:
I(t) is the current value in microamperes measured at time t;
$I_{SS}$ is the steady state current in microamperes;
$r_d$ is the radius of a microelectrode in centimeters; and
t is time in seconds.

3. The method of claim 2, wherein the calculating a hematocrit-corrected concentration of analyte step further comprises:
substituting the estimated diffusion coefficient into an equation of the form:

$$C_{red} = \frac{I_S}{4nFDr_d}$$

where:
$C_{red}$ is a reduced mediator concentration;
$I_{SS}$ is the steady state current in microamperes;
n is the number of electrons exchanged per ion that undergoes an oxidation/reduction reaction;
F is Faraday's constant;
D is the estimated diffusion coefficient in centimeter/second; and
$r_d$ is the radius of the microelectrode in centimeters;
generating a calibration curve in which a y-axis is the reduced mediator concentration and an x-axis is a reference analyte concentration;
calculating an analyte concentration by subtracting a calibration intercept from the reduced mediator concentration and dividing with a calibration slope.

4. The method of claim 1, wherein the test strip further comprises an insulation portion disposed on the plurality of microelectrodes and the insulation portion has a height between about one micron and about six microns.

5. The method of claim 1, wherein the reference electrode and the working electrode are comprised of gold.

6. The method of claim 1, wherein the reagent layer comprises an enzyme, a mediator and a buffering agent wherein the mediator comprises ruthenium (III) hexamine.

7. The method of claim 1, wherein the diameter of each of the plurality of microelectrodes is between about 5 microns and about 50 microns.

8. The method of claim 1, wherein each of the plurality of microelectrodes is spaced apart by a distance ranging from about 5 to about 10 times the diameter of a microelectrode.

9. The method of claim 1, wherein each of the plurality of microelectrodes is spaced apart by a distance ranging from about 25 microns to about 500 microns.

10. The method of claim 1, wherein the shape of each of the plurality of microelectrodes is selected from a group consisting of a circle, a square, a rectangle, an oval and an ellipse.

11. A system comprising:
a test strip having a reference electrode and a working electrode, wherein the working electrode formed with a plurality of microelectrodes and coated with an reagent layer and wherein the test strip further comprises an insulation portion disposed on the plurality of microelectrodes; and
a test meter comprising:
an electronic circuit for applying a test voltage between the reference electrode and the working electrode; and
a signal processor for measuring a test current and for calculating an effective diffusion coefficient.

12. The system of claim 11, wherein the insulation portion has a height between about one micron and about six microns.

13. The system of claim 11, wherein the effective diffusion coefficient is calculated from the slope of the linearly regressed plot $$\frac{I(t)}{I_{SS}}$$

$$\frac{1}{\sqrt{t}}$$

versus based on an equation of the form:

$$\frac{I(t)}{I_{SS}} = 1 + \left(\frac{2r_d}{\pi\sqrt{\pi Dt}}\right)$$

where:
I(t) is the test current in microamperes measured at time t;
$I_{SS}$ is a steady state current in microamperes;
$r_d$ is a radius of a microelectrode in centimeters; and
t is time in seconds.

14. The system of claim 13, wherein a hematocrit-corrected glucose concentration is calculated by using the estimated diffusion coefficient and an equation of the form:

$$C_{red} = \frac{I_S}{4nFDr_d}$$

where:
$C_{red}$ is a reduced mediator concentration;
$I_{SS}$ is the steady state current in microamperes;
n is the number of electrons exchanged per ion that undergoes an oxidation/reduction reaction;
F is Faraday's constant;
D is a estimated diffusion coefficient in centimeter/second; and
$r_d$ is a radius of the microelectrode in centimeters.

15. The system of claim 11, wherein an effective diffusion coefficient is used to discriminate between a fluid sample of whole blood and a fluid sample of control solution by comparing the effective diffusion coefficient to an acceptance range for whole blood and an acceptance range for control solution and the effective diffusion coefficient is used to determine if a test strip is formed with a plurality of microelectrodes by substituting the effective diffusion coefficient into an equation of the form:

$$\tilde{D} = D\exp\left\{\theta\left(\frac{1}{T} - \frac{1}{T_0}\right)\right\}$$

Where:
$\tilde{D}$ is a temperature-corrected effective diffusion coefficient in centimeter²/second;
D is a estimated effective diffusion coefficient in centimeter²/second;
θ is a known constant for temperature-dependent diffusion;
T is a temperature in Kelvin of the fluid sample as measured by the test meter; and
$T_o$ is a reference temperature in degrees Kelvin.

* * * * *